United States Patent
Graf et al.

(10) Patent No.: US 7,098,356 B2
(45) Date of Patent: Aug. 29, 2006

(54) SUBSTITUTED INDENYL METAL COMPLEXES AND POLYMERIZATION PROCESS

(75) Inventors: David D. Graf, Midland, MI (US); Jorge Soto, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/503,828

(22) PCT Filed: Mar. 3, 2003

(86) PCT No.: PCT/US03/06315

§ 371 (c)(1),
(2), (4) Date: Aug. 6, 2004

(87) PCT Pub. No.: WO03/078483

PCT Pub. Date: Sep. 25, 2003

(65) Prior Publication Data

US 2005/0143536 A1 Jun. 30, 2005

Related U.S. Application Data

(60) Provisional application No. 60/364,706, filed on Mar. 14, 2002.

(51) Int. Cl.
*C08F 4/64* (2006.01)
*C07F 17/00* (2006.01)

(52) U.S. Cl. ............ 556/53; 526/133; 526/160; 526/161; 526/165; 526/943; 505/103; 505/152; 505/162

(58) Field of Classification Search ............... 526/133, 526/160, 161, 165, 943; 556/53; 502/103, 502/152, 162
See application file for complete search history.

(56) References Cited

U.S. PATENT DOCUMENTS

| | | | |
|---|---|---|---|
| 5,321,106 A | 6/1994 | LaPointe | |
| 5,374,696 A | 12/1994 | Rosen et al. | |
| 5,470,993 A | 11/1995 | Devore et al. | |
| 5,486,632 A | 1/1996 | Devore et al. | |
| 5,541,349 A | 7/1996 | Wilson et al. | |
| 5,703,187 A | 12/1997 | Timmers | |
| 5,721,185 A | 2/1998 | LaPointe et al. | |
| 5,866,704 A | 2/1999 | Nickias et al. | |
| 6,015,868 A | 1/2000 | Nickias et al. | |
| 6,034,022 A | 3/2000 | McAdon et al. | |
| 6,329,486 B1 | 12/2001 | Shankar et al. | |

FOREIGN PATENT DOCUMENTS

| | | |
|---|---|---|
| WO | WO97/15583 | 5/1997 |
| WO | WO97/19463 | 5/1997 |
| WO | WO98/06728 | 2/1998 |

Primary Examiner—Caixia Lu

(57) ABSTRACT

Metal complexes comprising a substituted inden-1-yl group or hydrogenated or partially hydrogenated derivative thereof, said group being substituted at least at the 2-position thereof with a $C_{4-30}$ ligand group containing a secondary or tertiary substitution pattern at the β-carbon thereof, polymerization catalysts; and olefin polymerization processes using the same are disclosed.

9 Claims, No Drawings

SUBSTITUTED INDENYL METAL COMPLEXES AND POLYMERIZATION PROCESS

CROSS REFERENCE STATEMENT

This application claims the benefit of U.S. Provisional Application No. 60/364,706, filed Mar. 14, 2002.

BACKGROUND OF THE INVENTION

This invention relates to a class of metal complexes containing a substituted indenyl ligand, and to polymerization catalysts derived from such complexes that are particularly suitable for use in a polymerization process for preparing homopolymers and copolymers of olefins or diolefins, including copolymers comprising two or more olefins or diolefins such as copolymers comprising an α-olefin and ethylene or a monovinyl aromatic monomer and ethylene.

Constrained geometry metal complexes and methods for their preparation are disclosed in U.S. Pat. No. 5,703,187. This publication also teaches the preparation of certain novel copolymers of ethylene and a hindered vinyl monomer, including monovinyl aromatic monomers, having a pseudo-random incorporation of the hindered vinyl monomer therein. Additional teachings of constrained geometry catalysts may be found in U.S. Pat. Nos. 5,321,106, 5,721,185, 5,374,696, 5,470,993, 5,541,349, and 5,486,632, as well as WO97/15583, and WO97/19463.

Metal complexes containing a substituted indenyl group substituted in 2 or 3 position with a substituent were previously disclosed in U.S. Pat. Nos. 6,015,868 and 5,866,704. Similar metal complexes containing heteroatom substituents were disclosed in WO98/06728, published Feb. 19, 1998. Certain highly active, polycyclic aromatic, metal complexes, especially derivatives of s-indacenyl or cyclopentaphenanthrenyl ligand groups are disclosed in U.S. Pat. Nos. 6,034,022 and 6,329,486.

Despite the advance in the art obtained by the foregoing metal complexes, catalysts possessing improved catalytic performance are still desired by the industry. In particular, it would be desirable to provide improved metal complexes that may be readily synthesized and possess improved catalyst performance.

SUMMARY OF THE INVENTION

According to the present invention there is provided a metal complex corresponding to the formula:

$$CpM(Z)_z(X)_x(T)_t(X')_{x'} \quad (I),$$

Cp is a substituted inden-1-yl or partially hydrogenated derivative thereof substituted at least at the 2-position thereof with a $C_{4-30}$ alkyl, aralkyl, or trihydrocarbylsilylhydrocarbyl group, or a Group 15 or 16 heteroatom containing derivative thereof, said group containing 2 or 3 non-hydrogen substituents at a β-position thereof;

M is a metal selected from Groups 3–10 or the Lanthanide series of the Periodic Table of the Elements;

Z is a divalent moiety of the formula -Z'Y— joining Cp and M, wherein,

Z' is $SiR^6{}_2$, $CR^6{}_2$, $SiR^6{}_2SiR^6{}_2$, $CR^6{}_2CR^6{}_2$, $CR^6{=}CR^6$, $CR^6{}_2SiR^6{}_2$, $BR^6$, or $GeR^6{}_2$, bound at the 1-position of Cp;

Y is —O—, —S—, —$NR^5$—, —$PR^5$—; —$NR^5{}_2$, or —$PR^5{}_2$;

$R^5$, independently each occurrence, is hydrocarbyl, trihydrocarbylsilyl, or trihydrocarbylsilylhydrocarbyl, said $R^5$ having up to 20 atoms other than hydrogen, and optionally two $R^5$ groups or $R^5$ together with Y form a ring system;

$R^6$, independently each occurrence, is hydrogen, or a member selected from hydrocarbyl, hydrocarbyloxy, silyl, halogenated alkyl, halogenated aryl, —$NR^5{}_2$, and combinations thereof, said $R^6$ having up to 30 non-hydrogen atoms, and optionally, two $R^6$ groups form a ring system;

X is hydrogen or a monovalent anionic ligand group having up to 60 atoms not counting hydrogen;

T independently each occurrence is a neutral ligating compound having up to 20 atoms, other than hydrogen, and optionally T and X are bonded together;

X' is a divalent anionic ligand group having up to 60 atoms other than hydrogen;

z is 0, 1 or 2;

x is 0, 1, 2, or 3;

t is a number from 0 to 2, and x' is 0 or 1.

The above compounds may exist as isolated crystals, as a mixture with other compounds, in the form of a solvated adduct, dissolved in a solvent, especially an organic liquid solvent, in the form of a dimer, or as a chelated derivative, especially wherein the chelating agent is an organic material such as ethylenediaminetetraacetic acid (EDTA).

Also, according to the present invention, there is provided a catalyst for olefin polymerization comprising:

A. i) a metal compound of formula (I), and
   ii) an activating cocatalyst, the molar ratio of i) to ii) being from 1:10,000 to 100:1, or
B. the reaction product formed by converting a metal compound of formula (I) to an active catalyst by use of an activating technique.

Further according to the present invention there is provided a process for the polymerization of olefins comprising contacting one or more $C_{2-20}$ olefins, including cyclic olefins, under polymerization conditions with a catalyst comprising:

A. i) a metal compound of formula (I), and
   ii) an activating cocatalyst, the molar ratio of i) to ii) being from 1:10,000 to 100:1, or
B. the reaction product formed by converting a metal compound of formula (I) to an active catalyst by use of an activating technique.

The present catalysts and polymerization processes are especially efficient for production of olefin homopolymers, copolymers of two or more olefins, in particular, copolymers of ethylene and a $C_{3-8}$ α-olefin or a vinylaromatic monomer, such as styrene, and interpolymers of three or more such polymerizable monomers over a wide range of polymerization conditions, and especially at elevated temperatures. They are especially useful for the formation of ethylene homopolymers and copolymers of ethylene and one or more $C_{3-8}$ α-olefins as well as copolymers of ethylene, propylene and a diene (EPDM copolymers). Examples of suitable diene monomers include ethylidenenorbornene, 1,4-hexadiene or similar conjugated or nonconjugated dienes.

The catalysts of this invention may also be supported on a solid material and used in olefin polymerization processes in a slurry or in the gas phase. The catalyst may be prepolymerized with one or more olefin monomers in situ in a polymerization reactor or in a separate process with intermediate recovery of the prepolymerized catalyst prior to the primary polymerization process. They may also be combined with one or more additional catalysts whether metallocene or conventional Ziegler-Natta catalysts and used together or sequentially in one or more than one polymerization reactors according to the present process. In addition to their use as polymerization catalysts, compounds according to the present invention may be used for hydroformulation, hydrogenation or oligomerization processes.

DETAILED DESCRIPTION OF THE INVENTION

All reference to the Periodic Table of the Elements herein shall refer to the Periodic Table of the Elements, published and copyrighted by CRC Press, Inc., 1995. Also, any reference to a Group or Groups shall be to the Group or Groups as reflected in this Periodic Table of the Elements using the IUPAC system for numbering groups. For purposes of United States patent practice, the contents of any patent, patent application or publication referenced herein is hereby incorporated by reference in its entirety, especially with respect to the disclosure of analytical or synthetic techniques and general knowledge in the art.

If appearing herein, the term "comprising" and derivatives thereof is not intended to exclude the presence of any additional component, step or procedure, whether or not the same is disclosed herein. In order to avoid any doubt, all compositions claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, excepting those that are not essential to operability. The term "consisting of", if used, excludes any component, step or procedure not specifically delineated or listed. The term "or", unless stated otherwise, refers to the listed members individually as well as in any combination.

As used herein the term "aromatic" refers to a polyatomic, cyclic, ring system containing $(4\delta+2)$ $\pi$-electrons, wherein $\delta$ is an integer greater than or equal to 1. The term "fused" as used herein with respect to a ring system containing two or more polyatomic, cyclic rings means that with respect to at least two rings thereof, at least one pair of adjacent atoms is included in both rings. The term, "β-position", refers to an atom of a multi-atomic group that is next adjacent to the "α-position", said α-position being the attachment point by means of which the group is joined to the remainder of the metal compound.

Preferred compounds of formula (I) of the invention are those corresponding to the formula:

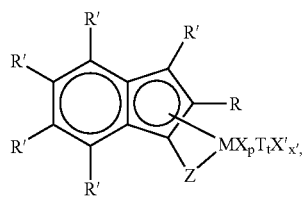

(II)

R' independently each occurrence is hydrogen, hydrocarbyl, trihydrocarbylsilyl, trihydrocarbylgermyl, halide, hydrocarbyloxy, trihydrocarbylsiloxy, bis(trihydrocarbylsilyl)amino, di(hydrocarbyl)amino, hydrocarbyleneamino, hydrocarbylimino, di(hydrocarbyl)phosphino, hydrocarbylenephosphino, hydrocarbylsulfido, halo-substituted hydrocarbyl, hydrocarbyloxy-substituted hydrocarbyl, trihydrocarbylsilyl-substituted hydrocarbyl, trihydrocarbylsiloxy-substituted hydrocarbyl, bis(trihydrocarbylsilyl)amino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said R' group having up to 40 atoms not counting hydrogen atoms, and two R' groups together may form a divalent derivative thereby forming a saturated or unsaturated ring;

R is a $C_{4-12}$ alkyl, aralkyl or trialkylsilylalkyl group containing 2 or 3 non-hydrogen substituents at the β-atom thereof;

M is a Group 4 metal;

Z is -Z'-Y—;

Y is —O—, —S—, —NR$^5$—, —PR$^5$—; —NR$^5{}_2$, or —PR$^5{}_2$;

Z' is SiR$^6{}_2$, CR$^6{}_2$, SiR$^6{}_2$SiR$^6{}_2$, CR$^6{}_2$CR$^6{}_2$, CR$^6$=CR$^6$, CR$^6{}_2$SiR$^6{}_2$, BR$^6$, or GeR$^6{}_2$;

R$^5$ each occurrence is independently hydrocarbyl, trihydrocarbylsilyl, or trihydrocarbylsilylhydrocarbyl, said R$^5$ having up to 20 atoms other than hydrogen, and optionally two R$^5$ groups or R$^5$ together with Y form a ring system;

R$^6$ each occurrence is independently hydrogen, or a member selected from hydrocarbyl, hydrocarbyloxy, silyl, halogenated alkyl, halogenated aryl, —NR$^5{}_2$, and combinations thereof, said R$^6$ having up to 20 non-hydrogen atoms, and optionally, two R$^6$ groups form a ring system;

X, T, and X' are as previously defined;

x is 0, 1 or 2;

t is 0 or 1; and x' is 0 or 1.

Examples of suitable R groups include: 2,2-dimethylpropan-1-yl, 2,2-dimethylbutan-1-yl, 2,2-diethylpropan-1-yl, 2,2-diethylbutan-1-yl, 2-methyl-2-phenylpropan-1-yl, benzyl, cyclohexylmethyl, trimethylsilylmethyl, and parafluorophenylmethyl groups, as well as Group 15 or 16 heteroatom containing groups of the formula:

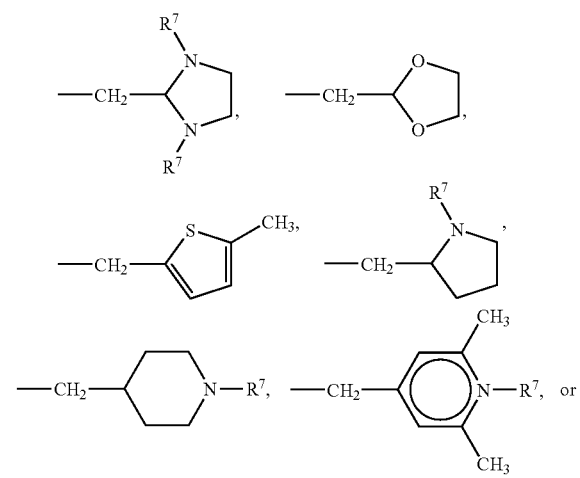

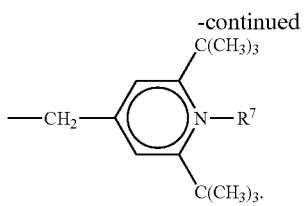

erein $R^7$ is hydrogen or $C_{1-10}$ alkyl, preferably hydrogen or methyl.

In a desirable embodiment, when x is 2, x' is zero, M is in the +4 formal oxidation state (or M is in the +3 formal oxidation state if Y is $-NR^5_2$ or $-PR^5_2$), and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy-, and di(hydrocarbyl)phosphino-substituted derivatives thereof, said X group having up to 30 atoms not counting hydrogen, when x is 0 and x' is 1, M is in the +4 formal oxidation state, and X' is a dianionic ligand selected from the group consisting of hydrocarbadiyl, oxyhydrocarbylene, and hydrocarbylenedioxy groups, said X group having up to 30 nonhydrogen atoms, when x is 1, and x' is 0, M is in the +3 formal oxidation state, and X is a stabilizing anionic ligand group selected from the group consisting of allyl, 2-(N,N-dimethylamino)phenyl, 2-(N,N-dimethylaminomethyl)phenyl, and 2-(N,N-dimethylamino)benzyl, and when x and x' are both 0, t is 1, M is in the +2 formal oxidation state, and T is a neutral, conjugated or nonconjugated diene, optionally substituted with one or more hydrocarbyl groups, said T having up to 40 carbon atoms and being bound to M by means of delocalized π-electrons thereof.

In the metal complexes, preferred T groups are carbon monoxide; phosphines, especially trimethylphosphine, triethylphosphine, triphenylphosphine and bis(1,2-dimethylphosphino)ethane; $P(OR^4)_3$, wherein $R^4$ is $C_{1-20}$ hydrocarbyl; ethers, especially tetrahydrofuran; amines, especially pyridine, bipyridine, tetramethylethylenediamine (TMEDA), and triethylamine; olefins; and neutral conjugated dienes having from 4 to 40, preferably 5 to 40 carbon atoms. Complexes including neutral diene T groups are those wherein the metal is in the +2 formal oxidation state.

Further in reference to the metal complexes, X preferably is desirably selected from the group consisting of hydro, halo, hydrocarbyl, silyl, and N,N-dialkylamino-substituted hydrocarbyl. The number of X groups depends on the oxidation state of M, whether Z is divalent or not and whether any neutral diene groups or divalent X' groups are present. The skilled artisan will appreciate that the quantity of the various substituents and the identity of Z are chosen to provide charge balance, thereby resulting in a neutral metal complex. For example, when Z is divalent, and x is zero, x' is two less than the formal oxidation state of M. When Z contains one neutral two electron coordinate-covalent bonding site, and M is in a formal oxidation state of +3, x may equal zero and x' equal 1, or x may equal 2 and x' equal zero. In a final example, if M is in a formal oxidation state of +2, Z may be a divalent ligand group, whereupon x and x' are both equal to zero and one neutral T ligand group may be present.

Most highly preferably, R' each occurrence is hydrogen, Z is $NR^5$ wherein $R^5$ is $C_{1-10}$ alkyl or cycloalkyl, preferably t-butyl; and Z' is dimethylsilane;

and, when x is 2, t and x' are both zero, M is in the +4 formal oxidation state, and X is independently each occurrence methyl, benzyl, or halide;

when x and t are zero, x' is one, and M is in the +4 formal oxidation state, X' is $-CH_2Si(CH_3)_2CH_2-$ or a 1,4-butenediyl group that forms a metallocyclopentene ring with M, when x is 1, t and x' are zero, M is in the +3 formal oxidation state, and X is 2-(N,N-dimethylamino)benzyl; and when x and x' are 0, t is 1, M is in the +2 formal oxidation state, and T is 1,4-diphenyl-1,3-butadiene or 1,3-pentadiene.

Specific examples of metal complexes of formula (I) according to the present invention include:

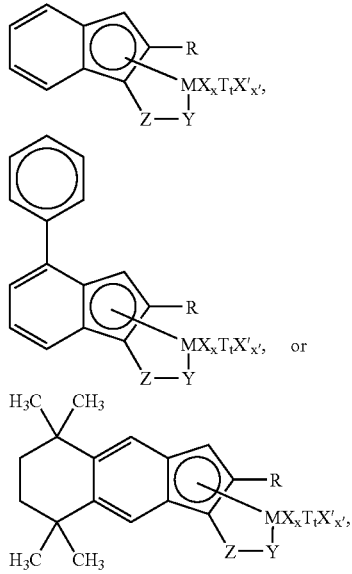

wherein

M is titanium;

R is 2,2-dimethylpropan-1-yl, 2-methyl-2-phenylpropan-1-yl, benzyl, or parafluorophenylmethyl;

Y is $-O-$, $-S-$, $-NR^5-$, $-PR^5-$; $-NR^5_2$, or $-PR^5_2$;

Z' is $SiR^6_2$, $CR^6_2$, $SiR^6_2SiR^6_2$, $CR^6_2CR^6_2$, $CR^6=CR^6$, $CR^6_2SiR^6_2$, $BR^6$, or $GeR^6_2$;

$R^5$ each occurrence is independently hydrocarbyl, trihydrocarbylsilyl, or trihydrocarbylsilylhydrocarbyl, said $R^5$ having up to 20 atoms other than hydrogen, and optionally two $R^5$ groups or $R^5$ together with Y form a ring system;

$R^6$ each occurrence is independently hydrogen, or a member selected from hydrocarbyl, hydrocarbyloxy, silyl, halogenated alkyl, halogenated aryl, $-NR^5_2$, and combinations thereof, said $R^6$ having up to 20 non-hydrogen atoms, and optionally, two $R^6$ groups form a ring system;

X, T, and X' are as previously defined;

x is 0, 1 or 2;

t is 0 or 1; and x' is 0 or 1;

and, when x is 2, x' is zero, M is in the +4 formal oxidation state (or M is in the +3 formal oxidation state if Y is $-NR^5_2$ or $-PR^5_2$), and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy-, and di(hydrocarbyl)phosphino-substituted derivatives thereof, said X group having up to 30 atoms not counting hydrogen, when x is 0 and x' is 1, M is in the +4 formal oxidation state, and X' is a dianionic ligand selected from the group consisting of hydrocarbadiyl, oxyhydrocarbylene, and hydrocarbylenedioxy groups, said X group having up to 30 nonhydrogen atoms, when x is 1, and x' is 0, M is in the +3 formal oxidation state, and X is a stabilizing anionic ligand group selected from the group consisting of allyl, 2-(N,N-dimethylaniino) phenyl, 2-(N,N-dimethylaminomethyl)phenyl, and 2-(N,N-dimethylamino)benzyl, and when x and x' are both 0, t is 1, M is in the +2 formal oxidation state, and T is a neutral, conjugated or nonconjugated diene, optionally substituted with one or more hydrocarbyl groups, said T having up to 40 carbon atoms and being bound to M by means of delocalized π-electrons thereof.

Most highly preferably, Y is $NR^5$ wherein $R^5$ is $C_{1-10}$ alkyl or cycloalkyl, preferably t-butyl; and Z' is dimethylsilane;

and, when x is 2, t and x' are both zero, M is in the +4 formal oxidation state, and X is independently each occurrence methyl, benzyl, or halide;

when x and t are zero, x' is one, and M is in the +4 formal oxidation state, X' is a 1,4-butadienyl group that forms a metallocyclopentene ring with M, when x is 1, t and x' are zero, M is in the +3 formal oxidation state, and X is 2-(N,N-dimethylamino)benzyl; and when x and x' are 0, t is 1, M is in the +2 formal oxidation state, and T is 1,4-diphenyl-1,3-butadiene or 1,3-pentadiene.

The metal complexes can be prepared by combining a metal halide salt with the corresponding indenyl ligand dianion in an inert diluent, or by combining a metal amide with the corresponding neutral indene ring system in an inert diluent. Optionally a reducing agent can be employed to produce the lower oxidation state complexes, and standard ligand exchange procedures, such as a halogenating agent can by used to produce different ligand substituents. Processes that are suitably adapted for use herein are well known to synthetic organometallic chemists. The syntheses are preferably conducted in a suitable noninterfering solvent at a temperature from −100 to 300° C., preferably from −78 to 100° C., most preferably from 0 to 50° C. By the term "reducing agent" herein is meant a metal or compound which, under reducing conditions causes the metal M, to be reduced from a higher to a lower oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, lithium or potassium alkadienyls; and Grignard reagents. Most preferred reducing agents are the alkali metals or alkaline earth metals, especially lithium and magnesium metal.

Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof, aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable.

Illustrative metal complexes according to the present invention include:

(2-neopentylinden-1-yl)-N-(1,1-dimethylethyl)dimethylsilanamide titanium (IV) dimethylenedimethylsilane,
(2-neopentylinden-1-yl)-N-(1,1-dimethylethyl)dimethylsilanamide titanium (II) 1,3-pentadiene,
(2-neopentylinden-1-yl)-N-(1,1-dimethylethyl)dimethylsilanamide titanium (II) 2-(N,N-dimethylamino)benzyl,
(2-neopentylinden-1-yl)-N-(1,1-dimethylethyl)dimethylsilanamide titanium (IV) dichloride,
(2-neopentylinden-1-yl)-N-(1,1-dimethylethyl)dimethylsilanamide titanium (IV) dimethyl,
(2-neopentylinden-1-yl)-N-(1,1-dimethylethyl)dimethylsilanamide titanium (IV) dibenzyl,
(2-(parafluorophenylmethyl)inden-1-yl)-N-(1,1-dimethylethyl)dimethylsilanamide titanium (I) dimethylenedimethylsilane,
(2-(parafluorophenylmethyl)inden-1-yl)-N-(1,1-dimethylethyl)dimethylsilanamide titanium (II) 1,3-pentadiene,
(2-(parafluorophenylmethyl)inden-1-yl)-N-(1,1-dimethylethyl)dimethylsilanamide titanium (II) 2-(N,N-dimethylamino)benzyl,
(2-(parafluorophenylmethyl)inden-1-yl)-N-(1,1-dimethylethyl)dimethylsilanamide titanium (I) dichloride,
(2-(parafluorophenylmethyl)inden-1-yl)-N-(1,1-dimethylethyl)dimethylsilanamide titanium (IV) dimethyl,
(2-(parafluorophenylmethyl)inden-1-yl)-N-(1,1-dimethylethy)dimethylsilanamide titanium (IV) dibenzyl,
(2-benzylinden-1-yl)-N-(1,1-dimethylethyl)dimethylsilanamide titanium (IV) dimethylenedimethylsilane,
(2-benzylinden-1-yl)-N-(1,1-dimethylethyl)dimethylsilanamide titanium (II) 1,3-pentadiene,
(2-benzylinden-1-yl)-N-(1,1-dimethylethyl)dimethylsilanamide titanium (III) 2-(N,N-dimethylamino)benzyl,
(2-benzylinden-1-yl)-N-(1,1-dimethylethyl)dimethylsilanamide titanium (IV) dichloride,
(2-benzylinden-1-yl)-N-(1,1-dimethylethyl)dimethylsilanamide titanium (IV) dimethyl,
(2-benzylinden-1-yl)-N-(1,1-dimethylethyl)dimethylsilanamide titanium (IV) dibenzyl,
(2-(2,2diethyl-1-butylinden-1-yl)-N-(1,1-dimethylethyl) dimethylsilanamide titanium (IV) dimethylenedimethylsilane,
(2-(2,2-dimethyl-1-butylinden-1-yl)-N-(1,1-dimethylethyl) dimethylsilanamide titanium (II) 1,3-pentadiene,
(2-(2,2-dimethyl-1-butylinden-1-yl)-N-(1,1-dimethylethyl) dimethylsilanamide titanium (III) 2-(N,N-dimethylamino)benzyl,
(2-(2,2-dimethyl-1-butylinden-1-yl)-N-(1,1-dimethylethyl) dimethylsilanamide titanium (IV) dichloride,
(2-(2,2-dimethyl-1-butylinden-1-yl)-N-(1,1-dimethylethyl) dimethylsilanamide titanium (IV) dimethyl,
(2-2,2-dimethyl-1-butylinden-1-yl)-N-(1,1-dimethylethyl) dimethylsilanamide titanium (IV) dibenzyl, and mixtures thereof, especially mixtures of positional isomers.

The skilled artisan will recognize that additional members of the foregoing list, obtainable by substitution of known ligands or different Group 3–10 metals for those specifically named, are also included within the invention. Moreover, it should also be recognized that all possible electronic distributions within the molecule, such as $\eta^3$, $\eta^4$ or $\eta^5$ are intended to be included by the foregoing named compounds.

The complexes are rendered catalytically active by combination with an activating cocatalyst or use of an activating technique, such as those that are previously known in the art for use with Group 4 metal olefin polymerization complexes. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium salts of compatible, noncoordinating anions; bulk electrolysis (explained in more detail hereinafter); and combinations of the foregoing activating cocatalysts and techniques. A preferred ion forming compound is a tri($C_{1-20}$-hydrocarbyl)ammonium salt of a tetrakis(fluoroaryl)borate, especially a tetrakis(pentafluorophenyl)borate. The foregoing activating cocatalysts and activating techniques have been previously taught with respect to different metal complexes in the following references: EP-A-277,003, U.S. Pat. No. 5,153,157, U.S. Pat. No. 5,064,802, U.S. Pat. No. 5,321,106, U.S. Pat. No. 5,721,185, U.S. Pat. No. 5,350,723, U.S. Pat. No. 5,425,872, U.S. Pat. No. 5,625,087, U.S. Pat. No. 5,883,204, U.S. Pat. No. 5,919,983, U.S. Pat. No. 5,783,512, WO 99/15534, and U.S. Ser. No. 09/251,664, filed Feb. 17, 1999 (WO99/42467).

Combinations of neutral Lewis acids, especially the combination of a trialkylaluminum compound having from 1 to 4 carbons in each alkyl group and a halogenated tri(hydrocarbyl)boron compound having from 1 to 20 carbons in each hydrocarbyl group, especially tris(pentafluorophenyl)borane, further combinations of such neutral Lewis acid mixtures with a polymeric or oligomeric alumoxane, and combinations of a single neutral Lewis acid, especially tris (pentafluorophenyl)borane with a polymeric or oligomeric alumoxane are especially desirable activating cocatalysts. Preferred molar ratios of Group 4 metal complex:tris(pentafluoro-phenylborane:alumoxane are from 1:1:1 to 1:10:30, more preferably from 1:1:1.5 to 1:5:10.

Suitable ion forming compounds useful as cocatalysts in one embodiment of the present invention comprise a cation which is a Bronsted acid capable of donating a proton, and a compatible, noncoordinating anion, $A^-$. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gallium, niobium or tantalum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

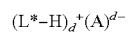

$(L^*-H)_d^+(A)^{d-}$ wherein:

L* is a neutral Lewis base;

$(L^*-H)^+$ is a conjugate Bronsted acid of L*;

$A^{d-}$ is a noncoordinating, compatible anion having a charge of d–, and d is an integer from 1 to 3.

More preferably $A^{d-}$ corresponds to the formula: $[M'Q_4]^-$;

wherein:

M' is boron or aluminum in the +3 formal oxidation state; and

Q independently each occurrence is selected from hydride, dialkylamido, halide, hydrocarbyl, hydrocarbyloxide, halo-substituted hydrocarbyl, halo-substituted hydrocarbyloxy, and halo-substituted silylhydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433.

In a more preferred embodiment, d is one, that is, the counter ion has a single negative charge and is $A^-$. Activating cocatalysts comprising boron which are particularly useful in the preparation of catalysts of this invention may be represented by the following general formula:

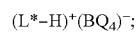

$(L^*-H)^+(BQ_4)^-$;

wherein:

L* is as previously defined;

B is boron in a formal oxidation state of 3; and

Q is a hydrocarbyl-, hydrocarbyloxy-, fluorohydrocarbyl-, fluorohydrocarbyloxy-, hydroxyfluorohydrocarbyl-, dihydrocarbylaluminumoxyfluorohydrocarbyl-, or fluorinated silylhydrocarbyl-group of up to 20 nonhydrogen atoms, with the proviso that in not more than one occasion is Q hydrocarbyl. Most preferably, Q is each occurrence a fluorinated aryl group, especially, a pentafluorophenyl group.

Preferred Lewis base salts are ammonium salts, more preferably trialkyl-ammonium- or dialkylarylammonium-salts containing one or more $C_{12-40}$ alkyl groups. The latter cocatalysts have been found to be particularly suitable for use in combination with not only the present metal complexes but other Group 4 metallocenes as well.

Illustrative, but not limiting, examples of boron compounds which may be used as an activating cocatalyst in the preparation of the improved catalysts of this invention (as well as previously known Group 4 metal catalysts) are tri-substituted ammonium salts such as:

trimethylammonium tetralis(pentafluorophenyl)borate,
triethylarnmonium tetrakis(pentafluorophenyl)borate, tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-dimethylanilinium n-butyltris(pentafluorophenyl)borate,
N,N-dimethylanilinium benzyltris(pentafluorophenyl)borate,
N,N-dimethylanilinium tetrakis(4-(t-butyldimethylsilyl)-2,3,5,6-tetrafluorophenyl)borate,
N,N-dimethylanilinium tetrakis(4-(triisopropylsilyl)-2,3,5,6-tetrafluorophenyl)borate,
N,N-dimethylanilinium pentafluorophenoxytris(pentafluorophenyl)borate,
N,N-diethylanilinium tetrakis(pentafluorophenyl)borate,
N,N-dimethyl-2,4,6-trimethylanilinium tetrakis(pentafluorophenyl)borate,
dimethyltetradecylammonium tetrakis(pentafluorophenyl)borate,
dimethylhexadecylammonium tetrakis(pentafluorophenyl)borate,
dimethyloctadecylammonium tetrakis(pentafluorophenyl)borate,
methylditetradecylammonium tetrakis(pentafluorophenyl)borate,
methylditetradecylammonium(hydroxyphenyl)tris(pentafluorophenyl)borate,
methylditetradecylammonium(diethylaluminoxyphenyl)tris(pentafluorophenyl)borate,
methyldihexadecylammonium tetrakis(pentafluorophenyl)borate,
methyldihexadecylammonium(hydroxyphenyl)trispentafluorophenyl)borate,
methyldihexadecylammonium(diethylaluminoxyphenyl)tris(pentafluorophenyl)borate,
methyldioctadecylammonium tetrakis(pentafluorophenyl)borate,
methyldioctadecylammonium(hydroxyphenyl)tris(pentafluorophenyl)borate,
methyldioctadecylammonium (diethylaluminoxyphenyl)tris(pentafluorophenyl)borate,
methyldioctadecylammonium tetrakis(pentafluorophenyl)borate,
phenyldioctadecylammonium tetrakis(pentafluorophenyl)borate,
phenyldioctadecylammonium(hydroxyphenyl)tris(pentafluorophenyl)borate,
phenyldioctadecylammonium (diethylaluminoxyphenyl)tris(pentafluorophenyl)borate,
(2,4,6-trimethylphenyl)dioctadecylammonium tetrakis(pentafluorophenyl)borate,
(2,4,6-trimethylphenyl)dioctadecylammonium(hydroxyphenyl)tris(pentafluorophenyl)-borate,
(2,4,6-trimethylphenyl)dioctadecylammonium(diethylaluminoxyphenyl) tris(pentafluorophenyl)borate,
(2,4,6-trifluorophenyl)dioctadecylammonium tetrakis(pentafluorophenyl)borate,
(2,4,6-trifluorophenyl)dioctadecylammonium(hydroxyphenyl)tris(pentafluorophenyl)-borate,
(2,4,6-trifluorophenyl)dioctadecylammonium(diethylaluminoxyphenyl)tris(pentafluoro-phenyl)borate,
(pentafluorophenyl)dioctadecylammonium tetrakis(pentafluorophenyl)borate,
(pentafluorophenyl)dioctadecylammonium (hydroxyphenyl)tris(pentafluorophenyl)-borate,
(pentafluorophenyl)dioctadecylammonium (diethylaluminoxyphenyl)tris(pentafluoro-phenyl) borate,
(p-trifluoromethylphenyl)dioctadecylammonium tetrakis (pentafluorophenyl)borate,
(p-trifluoromethylphenyl)dioctadecylammonium(hydroxyphenyl)tris(pentafluoro-phenyl)borate,
(p-trifluoromethylphenyl)dioctadecylammonium(diethylaluminoxyphenyl)tris(penta-fluorophenyl)borate,
p-nitrophenyldioctadecylammonium tetrakis(pentafluorophenyl)borate,
p-nitrophenyldioctadecylamnmonium(hydroxyphenyl)tris (pentafluorophenyl)borate,
p-nitrophenyldioctadecylammonium(diethylaluminoxyphenyl)tris(pentafluorophenyl)borate, and mixtures of the foregoing,
dialkyl ammonium salts such as:
di-(i-propyl)ammonium tetrakis(pentafluorophenyl)borate,
methyloctadecylammonium tetrakis(pentafluorophenyl)borate,
methyloctadodecylammonium tetrakis(pentafluorophenyl)borate, and
dioctadecylammonium tetrakis(pentafluorophenyl)borate;
tri-substituted phosphonium salts such as:
triphenylphosphonium tetrakis(pentafluorophenyl)borate,
methyldioctadecylphosphonium tetrakis(pentafluorophenyl)borate, and
tri(2,6-dimethylphenyl)phosphonium tetrakis(pentafluorophenyl)borate;
di-substituted oxonium salts such as:
diphenyloxonium tetrakis(pentafluorophenyl)borate,
di(o-tolyl)oxonium tetrakis(pentafluorophenyl)borate, and
di(octadecyl)oxonium tetrakis(pentafluorophenyl)borate;
di-substituted sulfonium salts such as:
di(o-tolyl)sulfonium tetrakis(pentafluorophenyl)borate, and
methylcotadecylsulfonium tetrakis(pentafluorophenyl)borate.

Preferred trialkylammonium cations are methyldioctadecylammonium and dimethyloctadecylammonium. The use of the above Bronsted acid salts as activating cocatalysts for addition polymerization catalysts is known in the art, having been disclosed in U.S. Pat. Nos. 5,064,802, 5,919,983, 5,783,512 and elsewhere. Preferred dialkylarylammonium cations are fluorophenyldioctadecylammonium-, perfluorophenyldioctacecylammonium- and p-trifluoromethylphenyldi(octadecyl)ammonium cations. It should be noted that certain of the cocatalysts, especially those containing a hydroxyphenyl ligand in the borate anion, may require the addition of a Lewis acid, especially a trialkylaluminum compound, to the polymerization mixture or the catalyst composition, in order to form the active catalyst composition.

Another suitable ion forming, activating cocatalyst comprises a salt of a cationic oxidizing agent and a noncoordinating, compatible anion represented by the formula:

$$(Ox^{e+})_d(A^{d-})_e.$$

wherein:
$Ox^{e+}$ is a cationic oxidizing agent having a charge of e+;
e is an integer from 1 to 3; and
$A^{d-}$ and d are as previously defined.

Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activating cocatalysts, especially tetrakis(pentafluorophenyl)borate. The use of the above salts as activating cocatalysts for addition polymerization catalysts is known in the art, having been disclosed in U.S. Pat. No. 5,321,106.

Another suitable ion forming, activating cocatalyst comprises a compound which is a salt of a carbenium ion and a noncoordinating, compatible anion represented by the formula:

©⁺A⁻ wherein:

©⁺ is a $C_{1-20}$ carbenium ion; and

A⁻ is as previously defined. A preferred carbenium ion is the trityl cation, that is triphenylmethylium. The use of the above carbenium salts as activating cocatalysts for addition polymerization catalysts is known in the art, having been disclosed in U.S. Pat. No. 5,350,723.

A further suitable ion forming, activating cocatalyst comprises a compound which is a salt of a silylium ion and a noncoordinating, compatible anion represented by the formula:

$R^3_3Si(X')_q^+A^-$ wherein:

$R^3$ is $C_{1-10}$ hydrocarbyl, and X', q and A⁻ are as previously defined.

Preferred silylium salt activating cocatalysts are trimethylsilylium tetrakispentafluorophenylborate, triethylsilylium tetrakispentafluorophenylborate and ether substituted adducts thereof. The use of the above silylium salts as activating cocatalysts for addition polymerization catalysts is known in the art, having been disclosed in U.S. Pat. No. 5,625,087.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

Another class of suitable catalyst activators are expanded anionic compounds corresponding to the formula: $(A^{1+a^1})_{b^1}(Z^1J^1_{j^1})^{-c^1}_{d^1}$, wherein:

$A^1$ is a cation of charge $+a^1$, $Z^1$ is an anion group of from 1 to 50, preferably 1 to 30 atoms, not counting hydrogen atoms, further containing two or more Lewis base sites;

$J^1$ independently each occurrence is a Lewis acid coordinated to at least one Lewis base site of $Z^1$, and optionally two or more such $J^1$ groups may be joined together in a moiety having multiple Lewis acidic functionality, $j^1$ is a number from 2 to 12 and $a^1$, $b^1$, $c^1$, and $d^1$ are integers from 1 to 3, with the proviso that $a^1 \times b^1$ is equal to $c^1 \times d^1$.

The foregoing cocatalysts (illustrated by those having imidazolide, substituted imidazolide, imidazolinide, substituted imidazolinide, benzimidazolide, or substituted benzimidazolide anions) may be depicted schematically as follows:

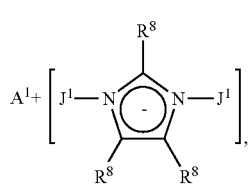

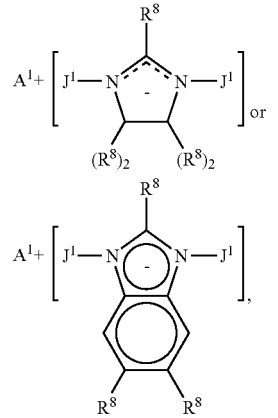

wherein:

$A^{1+}$ is a monovalent cation as previously defined, and preferably is a trihydrocarbyl ammonium cation, containing one or two $C_{10-40}$ alkyl groups, especially the methylbis (tetradecyl)ammonium- or methylbis(octadecyl)ammonium-cation, $R^8$, independently each occurrence, is hydrogen or a halo, hydrocarbyl, halocarbyl, halohydrocarbyl, silylhydrocarbyl, or silyl, (including mono-, di- and tri(hydrocarbyl)silyl) group of up to 30 atoms not counting hydrogen, preferably $C_{1-20}$ alkyl, and $J^1$ is tris(pentafluorophenyl)borane or tris(pentafluorophenyl)aluminane.

Examples of these catalyst activators include the trihydrocarbylammonium-, especially, methylbis(tetradecyl)ammonium- or methylbis(octadecyl)ammonium-salts of: bis (tris(pentafluorophenyl)borane)imidazolide, bis(tris (pentafluorophenyl)borane)-2-undecylimidazolide, bis(tris (pentafluorophenyl)borane)-2-heptadecylimidazolide, bis (tris(pentafluorophenyl)borane)-4,5-bis(undecyl) imidazolide, bis(tris(pentafluorophenyl)borane)-4,5-bis (heptadecyl)imidazolide, bis(tris(pentafluorophenyl)borane) imidazolinide, bis(tris(pentafluorophenyl)borane)-2-undecylimidazolinide, bis(tris(pentafluorophenyl)borane)-2-heptadecylimidazolinide, bis(tris(pentafluorophenyl) borane)-4,5-bis(undecyl)imidazolinide, bis(tris (pentafluorophenyl)borane)-4,5-bis(heptadecyl) imidazolinide, bis(tris(pentafluorophenyl)borane)-5,6-dimethylbenzimidazolide, bis(tris(pentafluorophenyl) borane)-5,6-bis(undecyl)benzimidazolide, bis(tris (pentafluorophenyl)alumane)imidazolide, bis(tris (pentafluorophenyl)alumane)-2-undecylimidazolide, bis(tris (pentafluorophenyl)alumane)-2-heptadecylimidazolide, bis (tris(pentafluorophenyl)alumane)-4,5-bis(undecyl) imidazolide, bis(tris(pentafluorophenyl)alumane)-4,5-bis (heptadecyl)imidazolide, bis(tris(pentafluorophenyl) alumane)imidazolinide, bis(tris(pentafluorophenyl) alumane)-2-undecyimidazohinide, bis(tris (pentafluorophenyl)alumane)-2-heptadecylimidazolinide, bis(tris(pentafluorophenyl)alumane)-4,5-bis(undecyl)imidazolinide, bis(tris(pentafluorophenyl)alumane)-4,5-bis (heptadecyl)imidazolinide, bis(tris(pentafluorophenyl)alumane)-5,6-dimethylbenzimidazolide, and bis(tris (pentafluorophenyl)alumane)-5,6-bis(undecyl) benzimidazolide.

A further class of suitable activating cocatalysts include cationic Group 13 salts corresponding to the formula:

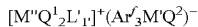

wherein:

M" is aluminum, gallium, or indium;

M' is boron or aluminum;

$Q^1$ is $C_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more $Q^1$ groups may be covalently linked with each other to form one or more fused rings or ring systems;

$Q^2$ is an alkyl group, optionally substituted with one or more cycloalkyl or aryl groups, said $Q^2$ having from 1 to 30 carbons;

L' is a monodentate or polydentate Lewis base, preferably L' is reversibly coordinated to the metal complex such that it may be displaced by an olefin monomer, more preferably L' is a monodentate Lewis base;

l' is a number greater than zero indicating the number of Lewis base moieties, L', and $Ar^f$ independently each occurrence is an anionic ligand group; preferably $Ar^f$ is selected from the group consisting of halide, $C_{1-20}$ halohydrocarbyl, and $Q^1$ ligand groups, more preferably $Ar^f$ is a fluorinated hydrocarbyl moiety of from 1 to 30 carbon atoms, most preferably $Ar^f$ is a fluorinated aromatic hydrocarbyl moiety of from 6 to 30 carbon atoms, and most highly preferably $Ar^f$ is a perfluorinated aromatic hydrocarbyl moiety of from 6 to 30 carbon atoms.

Examples of the foregoing Group 13 metal salts are alumicinium tris(fluoroaryl)borates or gallicinium tris(fluoroaryl)borates corresponding to the formula: $[M''Q^1{}_2L'_{1'}]^+ (Ar^f{}_3BQ^2)^-$, wherein M" is aluminum or gallium; $Q^1$ is $C_{1-20}$ hydrocarbyl, preferably $C_{1-8}$ alkyl; $Ar^f$ is perfluoroaryl, preferably pentafluorophenyl; and $Q^2$ is $C_{1-8}$ alkyl, preferably $C_{1-8}$ alkyl. More preferably, $Q^1$ and $Q^2$ are identical $C_{1-8}$ alkyl groups, most preferably, methyl, ethyl or octyl.

The foregoing activating cocatalysts may also be used in combination. An especially preferred combination is a mixture of a tri(hydrocarbyl)aluminum or tri(hydrocarbyl)borane compound having from 1 to 4 carbons in each hydrocarbyl group or an ammonium borate with an oligomeric or polymeric alumoxane compound.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris(pentafluorophenyl)borane, where used as an activating cocatalyst is employed in a molar ratio to the metal complex of form 0.5:1 to 10:1, more preferably from 1:1 to 6:1 most preferably from 1:1 to 5:1. The remaining activating cocatalysts are generally employed in approximately equimolar quantity with the metal complex.

The catalysts, whether or not supported in any suitable manner, may be used to polymerize ethylenically unsaturated monomers having from 2 to 100,000 carbon atoms either alone or in combination. Preferred addition polymerizable monomers for use herein include olefins, diolefins and mixtures thereof. Preferred olefins are aliphatic or aromatic compounds containing vinylic unsaturation as well as cyclic compounds containing ethylenic unsaturation. Examples of the latter include cyclobutene, cyclopentene, norbornene, and norbornene derivatives that are substituted in the 5- and 6-positions with $C_{1-20}$ hydrocarbyl groups. Preferred diolefins are $C_{4-40}$ diolefin compounds, including ethylidene norbornene, 1,4-hexadiene, norbornylene, and the like. The catalysts and processes herein are especially suited for use in preparation of ethylene/1-butene, ethylene/1-hexene, ethylene/styrene, ethylene/propylene, ethylene/1-pentene, ethylene/4-methyl-1-pentene and ethylene/1-octene copolymers as well as terpolymers of ethylene, propylene and a non-conjugated diene, such as, for example, EPDM terpolymers.

Most preferred monomers include the $C_{2-20}$ α-olefins, especially ethylene, propylene, isobutylene, 1-butene, 1-pentene, 1-hexene, 3-methyl-1-pentene, 4-methyl-1-pentene, 1-octene, 1-decene, long chain macromolecular α-olefins, and mixtures thereof. Other preferred monomers include styrene, $C_{1-4}$ alkyl substituted styrene, ethylidenenorbornene, 1,4-hexadiene, 1,7-octadiene, vinylcyclohexane, 4-vinylcyclohexene, divinylbenzene, and mixtures thereof with ethylene. Long chain macromolecular α-olefins are vinyl terminated polymeric remnants formed in situ during continuous solution polymerization reactions. Under suitable processing conditions such long chain macromolecular units are readily polymerized into the polymer product along with ethylene and other short chain olefin monomers to give small quantities of long chain branching in the resulting polymer.

Preferred monomers include a combination of ethylene and one or more comonomers selected from monovinyl aromatic monomers, 4-vinylcyclohexene, vinylcyclohexane, norbornylene, ethylidene-norbornene, $C_{3-10}$ aliphatic α-olefins (especially propylene, isobutylene, 1-butene, 1-hexene, 3-methyl-1-pentene, 4-methyl-1-pentene, and 1-octene), and $C_{4-40}$ dienes. Most preferred monomers are mixtures of ethylene and styrene; mixtures of ethylene, propylene and styrene; mixtures of ethylene, styrene and a nonconjugated diene, especially ethylidenenorbornene or 1,4-hexadiene, and mixtures of ethylene, propylene and a nonconjugated diene, especially ethylidenenorbornene or 1,4-hexadiene.

In general, the polymerization may be accomplished at conditions well known in the prior art for Ziegler-Natta or Kaminsky-Sinn type polymerization reactions, that is, temperatures from 0–250° C., preferably 30 to 200° C. and pressures from atmospheric to 10,000 atmospheres. Suspension, solution, slurry, gas phase, solid state powder polymerization or other process condition may be employed if desired. A support, especially silica, alumina, or a polymer (especially poly(tetrafluoroethylene) or a polyolefin) may be employed, and desirably is employed when the catalysts are used in a gas phase polymerization process. The support is preferably employed in an amount to provide a weight ratio of catalyst (based on metal):support from $1:10^6$ to $1:10^3$, more preferably from $1:10^6$ to $1:10^4$.

In most polymerization reactions the molar ratio of catalyst:polymerizable compounds employed is from $10^{-12}:1$ to $10^{-1}:1$, more preferably from $10^{-9}:1$ to $10^{-5}:1$.

Suitable solvents use for solution polymerization are liquids that are substantially inert under process conditions encountered in their usage. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and alkyl-substituted aromatic compounds such as benzene, toluene, xylene, and ethylbenzene. Suitable solvents also include liquid olefins which may act as monomers or comonomers.

The catalysts may be utilized in combination with at least one additional homogeneous or heterogeneous polymerization catalyst in the same reactor or in separate reactors connected in series or in parallel to prepare polymer blends having desirable properties. An example of such a process is disclosed in WO 94/00500.

The catalysts of the present invention are particularly advantageous for the production of ethylene homopolymers and ethylene/α-olefin copolymers having high levels of long chain branching. The use of the catalysts of the present invention in continuous polymerization processes, especially continuous, solution polymerization processes, allows for elevated reactor temperatures which favor the formation of vinyl terminated polymer chains that may be incorporated into a growing polymer, thereby giving a long chain branch. The use of the present catalyst compositions advantageously allows for the economical production of ethylene/α-olefin copolymers having processability similar to high pressure, free radical produced low density polyethylene.

The present catalyst compositions may be advantageously employed to prepare olefin polymers having improved processing properties by polymerizing ethylene alone or ethylene/α-olefin mixtures with low levels of a "H" branch inducing diene, such as norbornylene, 1,7-octadiene, or 1,9-decadiene. The unique combination of elevated reactor temperatures, high molecular weight (or low melt indices) at high reactor temperatures and high comonomer reactivity advantageously allows for the economical production of polymers having excellent physical properties and processabllity. Preferably such polymers comprise ethylene, a $C_{3-20}$ α-olefin and a "H"-branching comonomer. Preferably, such polymers are produced in a solution process, most preferably a continuous solution process.

The catalyst composition may be prepared as a homogeneous catalyst by addition of the requisite components to a solvent or diluent in which polymerization will be conducted. The catalyst composition may also be prepared and employed as a heterogeneous catalyst by adsorbing, depositing or chemically attaching the requisite components on an inorganic or organic particulated solid. Examples of such solids include, silica, silica gel, alumina, clays, expanded clays (aerogels), aluminosilicates, trialkylaluminum compounds, and organic or inorganic polymeric materials, especially polyolefins. In a preferred embodiment, a heterogeneous catalyst is prepared by reacting an inorganic compound, preferably a tri($C_{1-4}$ alkyl)aluminum compound, with an activating cocatalyst, especially an ammonium salt of a hydroxyaryl(trispentafluorophenyl)borate, such as an ammonium salt of (4-hydroxy-3,5-ditertiarybutylphenyl)tris(pentafluorophenyl)borate or (4-hydroxyphenyl)-tris(pentafluorophenyl)borate. This activating cocatalyst is deposited onto the support by coprecipitating, imbibing, spraying, or similar technique, and thereafter removing any solvent or diluent. The metal complex is added to the support, also by adsorbing, depositing or chemically attaching the same to the support, either subsequently, simultaneously or prior to addition of the activating cocatalyst.

When prepared in heterogeneous or supported form, the catalyst composition is employed in a slurry or gas phase polymerization. As a practical limitation, slurry polymerization takes place in liquid diluents in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise, the α-olefin monomer or a mixture of different α-olefin monomers may be used in whole or part as the diluent. Most preferably, at least a major part of the diluent comprises the α-olefin monomer or monomers to be polymerized. A dispersant, particularly an elastomer, may be dissolved in the diluent utilizing techniques known in the art, if desired.

At all times, the individual ingredients as well as the recovered catalyst components must be protected from oxygen and moisture. Therefore, the catalyst components and catalysts must be prepared and recovered in an oxygen and moisture free atmosphere. Preferably, therefore, the reactions are performed in the presence of an dry, inert gas, such as, for example, nitrogen.

The polymerization may be carried out as a batchwise or a continuous polymerization process. A continuous process is preferred, in which event catalyst, ethylene, comonomer, and optionally solvent, are continuously supplied to the reaction zone, and polymer product continuously removed therefrom.

Without limiting in any way the scope of the invention, one means for carrying out such a polymerization process is as follows: In a stirred-tank reactor, the monomers to be polymerized are introduced continuously, together with solvent and an optional chain transfer agent. The reactor contains a liquid phase composed substantially of monomers, together with any solvent or additional diluent and dissolved polymer. If desired, a small amount of a "H"-branch inducing diene such as norbornylene, 1,7-octadiene or 1,9-decadiene may also be added. Catalyst and cocatalyst are continuously introduced in the reactor liquid phase. The reactor temperature and pressure may be controlled by adjusting the solvent/monomer ratio, the catalyst addition rate, as well as by cooling or heating coils, jackets or both. The polymerization rate is controlled by the rate of catalyst addition. The ethylene content of the polymer product is determined by the ratio of ethylene to comonomer in the reactor, which is controlled by manipulating the respective feed rates of these components to the reactor. The polymer product molecular weight is controlled, optionally, by controlling other polymerization variables such as the temperature, monomer concentration, or by the previously mention chain transfer agent, such as a stream of hydrogen introduced to the reactor, as is well known in the art. The reactor effluent is contacted with a catalyst kill agent such as water. The polymer solution is optionally heated, and the polymer product is recovered by flashing off gaseous monomers as well as residual solvent or diluent at reduced pressure, and, if necessary, conducting further devolatilization in equipment such as a devolatilizing extruder. In a continuous process the mean residence time of the catalyst and polymer in the reactor generally is from 5 minutes to 8 hours, and preferably from 10 minutes to 6 hours.

Ethylene homopolymers and ethylene/α-olefin copolymers are particularly suited for preparation according to the invention. Generally such polymers have densities from 0.85 to 0.96 g/ml. Typically the molar ratio of α-olefin comonomer to ethylene used in the polymerization may be varied in order to adjust the density of the resulting polymer. When producing materials with a density range of from 0.91 to 0.93 the comonomer to monomer ratio is less than 0.2, preferably less than 0.05, even more preferably less than 0.02, and may even be less than 0.01. In the above polymerization process hydrogen has been found to effectively control the molecular weight of the resulting polymer. Typically, the molar ratio of hydrogen to monomer is less than 0.5, preferably less than 0.2, more preferably less than 0.05, even more preferably less than 0.02 and may even be less than 0.01.

EXAMPLES

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis. The term "overnight", if used, refers to a time of approximately 16–18 hours, "room temperature", if used, refers to a temperature of about 20–25° C., and "mixed alkanes" refers to a mixture of hydrogenated propylene oligomers, mostly $C_6$–$C_{12}$ isoalkanes, available commercially under the trademark Isopar E™ from Exxon Chemicals, Inc.

All solvents were purified using the technique disclosed by Pangborn et al, *Organometallics* 15, 1518–1520, (1996). $^1$H and $^{13}$C NMR shifts were referenced to internal solvent resonances and are reported relative to TMS. $^{19}$F NMR shifts were referenced to $CCl_3F$.

Example 1

(2-benzylinden-1-yl)-N-(1,1-dimethylethyl)dimethylsilanamide titanium (IV) dichloride

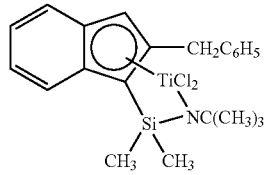

2-bromoindene. A 500 mL flask was charged with 25.5 g (120 mmol) of trans-2-bromo-1-indanol, 1 g of toluenesulfonic acid and 350 mL of toluene. This was capped with a Dean-Stark trap and heated to reflux for two hours at which time the system was cooled to room temperature and the volatiles removed in vacuo to leave a dark oil. The residue was taken up into hexanes and eluted through a silica pad using hexanes. Removal of the volatiles in vacuo gave 22.5 g (96 percent) of a light yellow oil.

$^1$H NMR ($C_6D_6$): δ 7.4–7.1 (m, 4H), 6.88 (s, 1H), 3.54 (s, 2H).

2-benzylindene. A 500 mL 3 neck flask was charged with 2.5 g (13 mmol) of 2-bromo-indene, 50 mg of $NiCl_2$(1,3-bis(diphenylphosphino)propane) (0.06 mmol) and 150 mL of diethyl ether. To this mixture was added dropwise 12.8 mL of 1.0 M benzyl magnesium chloride in ether (12.8 mmol). The reaction was heated to reflux overnight and then quenched by cooling to 0° C. and adding 150 mL of 1.0 M aqueous hydrochloric acid. The organic layer was separated and washed twice with 50 mL of ether. The organic extracts were combined, dried over magnesium sulfate, filtered and the volatiles removed in vacuo to leave a dark oil. The sample was dissolved in a small amount of hexanes and purified by flash column chromatography using silica and hexanes as the elutent. Yield: 1.75 g, 66 percent $^1$H NMR ($CDCl_3$): δ 7.6–7.1 (m, 9H), 6.60 (s, 1H), 3.89 (s, 2H), 3.36 (s, 2H);

$^{13}$C {$^1$H} NMR ($CDCl_3$) δ 149.58, 145.65, 143.76, 140.34, 129.30, 128.80, 128.14, 126.61, 126.54, 124.21, 123.80, 120.54, 41.14, 38.28

(2benzylinden-1-yl)-N-(1,1-dimethylethyl)dimethylsilanamine. A 125 mL flask was charged with 1.75 g (8.5 mmol) of 2-benzylindene and 50 mL of hexanes. To this was added over five minutes 5.6 mL of n-butyl lithium (8.9 mmol, 1.6 M in hexanes). After stirring for four hours, the suspension was filtered through diatomaceous earth and the isolated solid extracted into 75 mL of THF and to this added 1.6 g of N-(1,1-dimethylethyl)dimethyl-silanamine chloride in 20 mL of THF. After stirring overnight, the volatiles were removed in vacuo and the residue extracted into 100 mL of hexanes. The extract was filtered through diatomaceous earth and the volatiles removed in vacuo to leave 2.46 g of oil (86 percent).

$^1$H NMR ($C_6D_6$): δ 7.5–7.1 (m, 9H), 6.42 (s, 1H), 4.01 (d, 1H), 3.75 (d, 1H), 3.35 (s, 1H), 1.10 (s, 1H), 0.98 (s, 9H), 0.11 (s, 3H), –0.12 (s, 3H);

$^{13}$C {$^1$H} NMR ($C_6D_6$) δ 151.53, 145.58, 145.01, 140.79, 129.33, 128.85, 128.62, 126.52, 125.17, 123.69, 122.95, 120.48, 49.40/49.30, 38.38, 33.58, 1.51, –0.70.

(2-benzylinden-1-yl)-N-(1,1-dimethylethyl)dimethylsilanamide titanium (IV) dichloride. A 125 mL flask was charged with 2.46 g (7.3 mmol) of (2-benzylinden-1-yl)-N-(1,1-dimethylethyl)dimethylsilanamine and 50 mL of hexanes. To his was added over ten minutes 9.4 mL of n-butyl lithium in hexanes (15.0 mmol, 1.6M). After 1 hour, 60 mL of THF was added and the solution cooled to –30° C. To this was added 2.4 g of $TiCl_3(THF)_3$ and the solution allowed to warm to room temperature. After 45 minutes, 1 g of $PbCl_2$ and 15 mL of dichloromethane was added. The solution was allowed to stir at room temperature for three hours and the volatiles were removed in vacuo. The residue was extracted into 20 mL of hot diethyl ether, filtered and the solution cooled to room temperature and then to –30° C. The resulting solid was collected by filtration, washed twice with 5 mL of cold ether and dried in vacuo to leave 520 mg of powder (16 percent).

$^1$H NMR ($C_6D_6$): δ 7.60 (d, 1H), 7.2–6.8 (m, 8H), 6.98 (s, 1H), 4.10 (d, 1H), 3.9 (d, 1H), 1.33 (s, 9H), 0.48 (s, 3H), 0.40 (s, 3H).

Example 2

(2-benzylinden-1-yl)-N-(1,1-dimethylethyl)dimethylsilanamide titanium dimethyl

A 50 mL jar was charged with 110 mg (0.24 mmol) of (2-benzylinden-1-yl)-N-(1,1-dimethylethyl)dimethylsilanamide titanium (IV) dichloride and 15 mL of diethyl ether. The mixture was cooled to –30° C. and to this added 0.25 mL of methyl magnesium bromide (0.73 mmol, 3.0 M in ether). After stirring and warming to room temperature over 1 hour, the volatiles were removed in vacuo and the residue extracted into 30 mL of hexanes. The extract was filtered through diatomaceous earth and the volatiles removed in vacuo. The residue was extracted into 20 mL of hexanes, filtered and the volatiles removed in vacuo to leave 86 mg of material (86 percent).

$^1$H NMR ($C_6D_6$): δ 7.51 (d, 1H), 7.38 (d, 1H), 7.2–6.9 (m, 6H), 6.85 (m, 1H), 6.80 (s, 1H), 3.83 (d, 1H), 3.66 (d, 1H), 1.46 (s, 9H), 0.88 (s, 3H), 0.48 (s, 3H), 0.41 (s, 3H), –0.13(s, 3H).

$^{13}$C {$^1$H} NMR (C$_6$D$_6$) δ 143.98, 140.79, 134.54, 132.02, 128.81, 128.55, 127.89, 127.57, 126.31, 125.67, 125.63, 125.34, 116.31, 58.15, 57.27, 52.26, 38.01, 34.25, 5.98, 5.61.

Example 3

(2-(cyclohexylmethyl)inden-1-yl)-N-(1,1-dimethylethyl) dimethylsilanamide titanium (IV) dichloride

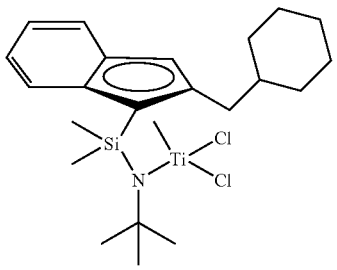

2-(cyclohexylmethyl)indene. To a suspension of freshly ground magnesium turnings (0.40 g, 16 mmol) in 100 mL of ether was added about 20 percent of a 100 ml ether solution containing 2.5 g (14 mmol) of bromo-methyl-cyclohexane. The reaction was heated to reflux and the remaining bromo-methyl-cyclohexane solution added over one hour. After 1 hour, an additional 150 mg of freshly ground Mg was added and after 5 hours, the mixture was cooled to room temperature. The Grignard solution was added over one hour to a mixture of 2.45 g (13 mmol) of 2-bromo-indene, 100 mg of NiCl$_2$(dppp) (0.15 mmol) and 100 mL of ether. The system was gently heated to reflux overnight and then cooled and quenched by adding 150 mL of 1.0 M aqueous hydrochloric acid. The product was isolated and purified (hexanes/silica) as for 2-benzyl-indene.

Yield: 2.05 g, 68 percent.

$^1$H NMR (CDCl$_3$): δ 7.3–6.9 (m, 4H), 6.40 (s, 1H), 3.05 (s, 2H), 2.15 (m, 2H), 1.6 (m, 5H), 1.4–1.0 (m, 4H), 0.8 (m, 2H).

(2-(cyclohexylmethyl)inden-1-yl)-N-(1,1-dimethylethyl) dimethylsilanamine. To a mixture of 2-(cyclohexylmethyl) indene (2.0 g, 9.4 mmol) in 40 mL of hexanes were added 6.0 mL of butyl lithium (1.6 M hexane; 9.6 mmol). The mixture was stirred overnight, the mother liquor decanted and the solid dissolved in THF. To this was added N-(1,1-dimethylethyl)dimethylsilanamine chloride (1.64 g, 9.9 mmol) and the solution stirred for 1 hour. The volatiles were removed in vacuo, the residue extracted with hexane, filtered and the volatiles removed in vacuo to give 2.85 g (90 percent) of a yellow oil.

$^1$H NMR (C$_6$D$_6$): δ 7.5 (d, 2H), 7.4 (d, 2H), 7.35–7.10 (m, 2H), 6.55 (s, 1H), 3.35 (s, 1H), 2.6 (d, 1H), 2.4 (d, 1H), 1.9–1.4 (m, 4H), 1.3–0.6, (m, 21 H), 0.13 (s, 3H), −0.11 (s, 3H);

$^{13}$C {$^1$H} NMR (C$_6$D$_6$) δ 151.46, 145.34, 125.83, 125.14, 123,83, 123.67, 122.65, 120.17, 49.53, 39.96, 38.34, 33.69, 33.63, 33.52, 26.85, 26.75, 1.20, −0.50

(2-(cyclohexylmethyl)inden-1-yl)-N-(1,1-dimethylethyl) dimethylsilanamide titanium (IV) dichloride. A 125 mL flask was charged with 2.54 g (7.6 mmol) of (2-(cyclohexylmethyl)inden-1-yl)-N-(1,1-dimethylethyl)dimethylsilanamine and 30 mL of hexanes. To this was added over five minutes 9.5 mL of n-butyl lithium in hexanes (15.1 mmol, 1.6M). After 1 hour, 50 mL of THF was added and the solution cooled to −30° C. To this was added 2.84 g (7.6 mmol) of TiCl$_3$(THF)$_3$ and the solution allowed to warm to room temperature. After 45 minutes, 2.1 g (7.6 mmol) of PbCl$_2$ and 10 mL of dichloromethane was added. The solution was allowed to stir at room temperature for three hours and the volatiles were removed in vacuo. The residue was extracted into toluene, filtered and the volatiles removed in vacuo. The residue was extracted into hexanes, filtered and the solution concentrated to dryness. The residue was dissolved in 5 mL hexanes and 10 mL of octane added—the resulting suspension was cooled to −30° C. overnight. The precipitate was isolated by decanting the mother liquor and the solid washed twice with 2 mL of cold octane. The solid was dried in vacuo to leave 490 mg of orange powder (14 percent).

$^1$H NMR (C$_6$D$_6$): δ 7.62 (d, 1H), 7.29 (d, 1H), 7.04 (m, 1H), 6.89 (m, 1H), 6.87 (s, 1H), 2.6 (m, 2H), 1.8–0.6 (m, 11H), 1.33 (s, 9H), 0.55 (s, 3H1), 0.52 (s, 3H).

$^{13}$C {$^1$H} NMR (C$_6$D$_6$) δ 149.13, 136.72, 134.75, 128.59, 127.99, 127.31, 126.19, 121.91, 62.37, 41.54, 41.37, 33.79, 32.63, 32.24, 26.56, 26.532, 26.30, 5.41, 4.86.

Example 4

(2-(cyclohexylmethyl)inden-1-yl)-N-(1,1-dimethylethyl)dimethylsilanamide titanium (IV) dimethyl A 50 mL jar was charged with 116 mg (0.25 mmol) of (2-(cyclohexylmethyl)inden-1-yl)-N-(1,1-dimethylethyl) dimethylsilanamide titanium (IV) dichloride and 10 mL of diethyl ether. The mixture was cooled to −30° C. and to this added 0.30 mL of methyl magnesium bromide (0.85 mmol, 3.0 M in ether). After stirring and warming to room temperature over 1 hour, the volatiles were removed in vacuo and the residue extracted into 20 mL of hexanes. The extract was filtered through diatomaceous earth and the volatiles removed in vacuo. The residue was extracted into 20 mL of hexanes, filtered and the volatiles removed in vacuo to leave 85 mg of material (80 percent).

$^1$H NMR (C$_6$D$_6$): δ 7.54 (m, 2H), 7.05 (m, 1H), 6.87 (m, 2H), 2.47 (m, 1H), 1.16 (m, 1H), 1.8–0.7 (m, 11H), 1.47 (s, 9H), 0.86 (s, 3H), 0.56 (s, 6H), −0.12 (s, 3H).

$^3$C {$^1$H} NMR (C$_6$D$_6$) δ 145.86, 134.75, 131.87, 127.52, 125.55, 125.51, 125.13, 116.05, 58.02, 56.92, 52.17, 41.18, 40.59, 34.42, 34.27, 34.08, 32.80, 26.73, 26.67, 26.41, 6.26, 5.73.

Example 5

(2-(p-fluorophenylmethyl)inden-1-yl)-N-(1,1-dimethylethyl)dimethyl-silanamide titanium (IV) dichloride

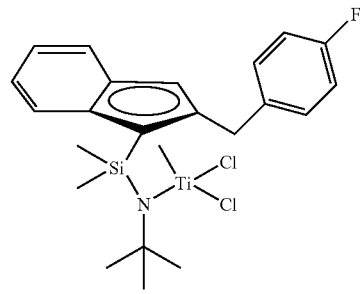

2-(4-fluorophenylmethyl)indene. To a suspension of freshly ground magnesium (0.58 g, 23 mmol) in 100 mL of ether was added about 3 mL of a 15 mL ether solution containing 3.0 g (21 mmol) of 4-fluorophenylmethyl chloride. The system was carefully heated and after initiation of the reaction, the remaining chloride solution added over 30 minutes while maintain a gentle reflux. After refluxing for 1.5 hours, the Grignard solution was cooled and cannulated to a mixture of 3.65 g (19 mmol) of 2-bromo-indene, 150 mg (0.20 mmol) of $NiCl_2(dppp)$ and 100 mL of ether. The system was gently heated to reflux overnight and then cooled and quenched by adding 150 mL of 1.0 M aqueous hydrochloric acid. The product was isolated and purified (hexanes/silica) as for 2-benzyl-indene. Yield: 3.45 g, 74 percent $^1H$ NMR ($C_6D_6$): δ 7.25–7.0 (m, 3H), 7.07 (m, 1H), 6.74 (m, 4H), 6.24 (s, 1H), 3.30 (s, 2H), 2.84 (s, 2H);

$^{13}C$ {$^1H$} NMR ($C_6D_6$) δ 163.46, 145.50, 143.58, 135.83, 135.79, 130.47, 130.37, 128.21, 126.62, 124.30, 123.65, 120.51, 115.46, 115.18, 40.64, 36.93;

$^{19}F$ NMR ($C_6D_6$): δ −117.30 (m)

(2-(4-fluorophenylmethyl)inden-1-yl)-N-(1,1-dimethylethyl)dimethylsilanamine. To a mixture of 2-(4-fluorophenylmethyl)indene (2.21 g, 9.9 mmol) in 45 mL of hexanes were added 6.5 mL of butyl lithium (1.6 M hexane; 10.4 mmol). The mixture was stirred overnight, the mother liquor decanted and the solid dissolved in THF. To this was added N-(1,1-dimethylethyl)dimethylsilanamine chloride (1.80 g, 10.8 mmol) and the reaction heated at reflux for three hours. The volatiles were removed in vacuo, the residue extracted with hexane, filtered and the volatiles removed in vacuo to give 3.39 g (97 percent) of a yellow oil.

$^1H$ NMR ($C_6D_6$): δ 7.42 (d, 1H), 7.40–7.00 (m, 4H), 7.00–6.7 (m, 6H), 6.38 (s, 1H), 3.38 (d, 1H), 3.63 (d, 1H), 3.35 (s, 1H), 0.98 (s, 9H), 0.10 (s, 3H), −0.13 (s, 3H);

$^{13}C$ {$^1H$} NMR ($C_6D_6$): δ 151.26, 145.50, 144.85, 130.70, 126.99, 125.23, 124.39, 124.28, 123.66, 123.07, 120.49, 115.30, 49.27, 37.44, 33.58, 1.45, −0.74;

$^{19}F$ NMR ($C_6D_6$): δ −117.30 (m).

(2-(4-fluorophenylmethyl)inden-1-yl)-N-(1,1-dimethylethyl)dimethyl-silanamide titanium (IV) dichloride. A 50 mL jar was charged with 2.50 g (7 mmol) (2-(4-fluorophenylmethyl)inden-1-yl)-N-(1,1-methylethyl)dimethylsilanamine, 1.60 g of $It(NMe_2)_4$ and 25 mL of octane. The reaction was heated to reflux for 43 hrs and then cooled to room temperature. To this was added 15 mL of trimethylsilylchloride and the reaction stirred overnight. The volatiles were removed in vacuo, the residue extracted into ether (75 mL) and the filtered extract concentrated to about 20 mL. The solution was cooled to −30° C. The formed solid was collected by filtration and washed with 5 mL of cold ether. The solid was dried in vacuo to leave 1.03 g of material. A second crop (650 mg) was isolated by concentration of the mother liquor and cooling at −30° C. Total yield 1.68 g, 51 percent $^1H$ NMR ($C_6D_6$): δ 7.61 (d, 1H), 7.21 (d, 1H), 7.10–6.70 (m, 7H), 3.96 (d, 1H), 3.85 (d, 1H), 1.35 (s, 9H), 0.52 (s, 3H), 0.38 (s, 3H);

$^{13}C$ {$^1H$} NMR ($C_6D_6$) δ 163.54, 146.74, 136.60, 135.62, 135.57, 130.32, 130.215, 128.76, 128.22, 127.24, 126.30, 122.16, 115.59/115.31, 62.60, 40.48, 37.93, 32.20, 5.12, 4.67;

$^{19}F$ NMR ($C_6D_6$): δ −116.56 (m).

Example 6

(2-(p-fluorophenylmethyl)inden-1-yl)-N-(1,1-dimethylethyl)dimethyl-silanamide titanium (IV) dimethyl A 50 mL jar was charged with 220 mg (0.47 mmol) of (2-(4-fluorophenylmethyl)inden-1-yl)-N-(1,1-dimethylethyl)dimethylsilanamide titanium (IV) dichloride and 10 mL of diethyl ether. The mixture was cooled to −30° C. and to this added 0.5 mL of methyl magnesium bromide (1.4 mmol, 3.0 M in ether). After stirring and warming to room temperature over 1 hour, the volatiles were removed in vacuo and the residue extracted into 30 mL of hexanes. The extract was filtered through diatomaceous earth and the volatiles removed in vacuo. The residue was extracted into 20 mL of hexanes, filtered and the volatiles removed in vacuo to leave 170 mg of material (75 percent).

$^1H$ NMR ($C_6D_6$): δ 7.50 (d, 1H), 7.40 (d, 1H), 7.03 (m, 1H), 6.85 (m, 3H), 6.76 (m, 3H), 3.69 (d, 1H), 3.51 (d, 1H), 1.45 (s, 9H), 0.84 (s, 3H), 0.49 (s, 3H), 0.36 (s, 3H), −0.14 (s, 3H).

$^{13}C$ {$^1H$} NMR ($C_6D_6$) δ 163.38, 160.15, 143.58, 136.41, 134.53, 131.95, 130.22/130.12, 127.54, 125.78, 125.58, 125.45, 116.18, 115.37, 115.10, 58.19, 57.55, 52.22, 37.07, 34.24, 5.97, 5.56;

$^{19}F$ NMR ($C_6D_6$): δ −117.20 (m)

Example 7

(2-(2-methyl-2-phenylpropan-1-yl)inden-1-yl)-N-(1,1-dimethylethyl)dimethylsilanamide titanium (IV) dichloride

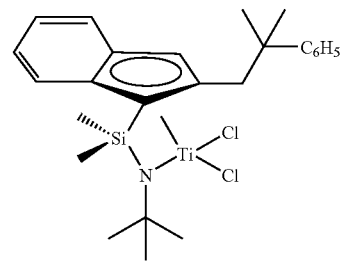

2-(2-methyl-2-phenylpropan-1-yl)indene. A mixture of 2-bromoindene (2.0 g, 10.2 mmol) and 460 mg of $Pd(AcO)_2$ in 60 mL of ether was treated with 21 mL of 2-methyl-2-phenyl-propanyl magnesium chloride (0.5 M in ether; 10.2 mmol). The mixture was refluxed for one hour, cooled to room temperature and treated with 30 mL of aqueous hydrochloric acid (5 percent). The reaction was worked-up and the product purified (hexanes/silica) as for 2-benzyl-indene. Yield: 1.6 g (63 percent).

$^1H$ (CDCl$_3$): δ 7.5 (br), 7.3 (br), 7.15 (m), 6.5 (s, 1H), 2.92 (s, 2H), 2.87 (s, 2H), 1.5(s, 6H), 1.3 (s, 2H);

$^{13}C${$^1H$} NMR (CDCl$_3$): δ 147.5, 145.2, 143.5, 129.6, 127.9, 126.0, 125.9, 125.7, 125.3, 123.6, 123.2, 119.9, 46.4, 42.4, 38.8, 38.4, 29.2.

(2-(2-methyl-2-phenyl propan-1-yl)inden-1-yl)-N-(1,1-dimethylethyl)dimethylsilanamine. To a mixture of 2-(2-methyl-2-phenyl propan-1-yl)indene (1.55 g, 6.2 mmol) in 50 mL of hexanes were added 4.0 mL of butyl lithium (1.6 M hexane; 1.02 equiv.). The mixture was stirred overnight, filtered, the solid was washed with hexanes and dried, recovering 1.05g (66 percent of indenyl lithium salt) of very pale yellowish solid. The solid was dissolved in THF and a solution of N-(1,1-dimethylethyl)dimethylsilanamine chloride (0.7 g, 1.03 equiv.; 4.2 mmol) in 20 mL of THF was added and the solution was stirred overnight. The volatiles were pumped off, the residue extracted with hexane, filtered and the filtrate was then dried in vacuo to give 1.5 g (96 percent) of a yellow oil.

$^1$H NMR (C$_6$D$_6$): δ 7.4 (d), 7.3 (d), 7.1 (m), 6.32 (s), 6.4 (d, 1H), 2.7–3.0 (misc. isomer peaks), 1.0 (s, 9H), −0.09 (s), −0.11 (s).

$^{13}$C {$^1$H} NMR (C$_6$D$_6$): δ 149.4, 145.4, 145.0, 128.3, 126.5, 126.4, 126.0, 125.1, 123.5, 120.3, 51.4, 46.4, 39.0, 33.8, 31.9, 29.8, 28.4, 23.0, 14.3, 0.8, 0.5, plus various isomer peaks (10–20 percent intensity of major isomer peaks).

(2-(2-methyl-2-phenylpropan-1-yl)inden-1-yl)-N-(1,1-dimethylethyl)dimethylsilanamide titanium (IV) dichloride. Into a 100 mL jar were placed 0.50 g (1.32 mmol) of (2-(2-methyl-2-phenyl propan-1-yl)inden-1-yl)-N-(1,1-dimethylethyl)dimethylsilanamine, 50 mL of hexane, and then 1.7 mL of n-butyl lithium (1.6M, hexanes) were added. The mixture was stirred overnight. A small amount of solid precipitates. The volatiles were removed in vacuo and the residues dissolved in 20 mL of THF. This was followed by addition of 0.49 g (1.32 mmol) of TiCl$_3$(THF)$_3$, the mixture was stirred for thirty minutes and then PbCl$_2$ (MW) 278.1: 260 mg, 1.3 electron equivalents) was added, followed by 5 mL of dichloromethane. After one hour the volatiles were removed in vacuo. The residue was dissolved in hexane (60 mL), filtered and the filtrate dried. Once again the residue was dissolved in hexane (20 mL), filtered and the filtrate concentrated down to about 2 mL, and the mixture was placed in the freezer. The material which separated from the mother liquor had identical spectrum as the residue from the mother liquor, so they were mixed again for a combined yield of 0.52 g of a dark red mass.

$^1$H NMR (C$_6$D$_6$): δ 7.6 (d), 7.1 (s), 6.95 (m), 6.85 (m), 6.4 (s), 3.3 and 2.9 (dd), 1.3 (s), 1.2 (s), 1.15 (s), 0.6 (s) 0.5 (s);

$^{13}$C {$^1$H} NMR (C$_6$D$_6$) δ 148.5, 147.0, 137.0, 135.0, 128.5, 127.1, 126.5, 126.4, 126.3, 122.0, 62.5, 47.6, 40.0, 32.3, 30.0, 27.1, 25.5, 6.1, 5.7.

Example 8

(2-(2-methyl-2-phenylpropan-1-yl)inden-1-yl)-N-(1,1-dimethylethyl)dimethylsilanamide titanium (IV) dimethyl Into a 120 mL jar were placed 0.52 g (1.0 mmol) of (2-(2-methyl-2-phenyl propan-1-yl)inden-1-yl)-N-(1,1-dimethylethyl)dimethylsilanamide titanium (IV) dichloride and 60 mL of ether. Then 0.74 mL of methyl magnesium iodide (3M, ether, 2.5 mmol) were added. The mixture was stirred for one hour, the volatiles removed in vacuo, the residue extracted with hexane, filtered (dark sticky, oily residue), and the filtrate concentrated down to about 2 mL. The solution was placed overnight in the −30° C. freezer. A small amount of an oily material precipitated, but since the NMR spectrum of this oil and that of the material left in the filtrate were essentially identical, they were combined for a total yield of 0.40 g of a very dark reddish-brown oil.

$^1$H NMR (C$_6$D$_6$): δ −0.2 (s, 3H), 0.54 (s, 3H), 0.56 (s, 3H), 0.8 (s, 3H), 1.28 (s, 3H), 1.3 (s, 3H), 1.45 (s, 9H), 2.8 (d, 2H), 6.5 (s, 1H), 6.85 (m), 7.0 (m), 7.0–7.2 (m), 7.3 (m), 7.5 (m).

Example 9

(2-neopentylinden-1-yl)-N-(1,1-dimethylethyl)dimethylsilanamide titanium (IV) dichloride

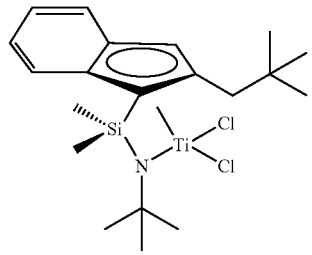

2-neopentylindene. To a mixture of 2-bromoindene (7.5 g, 39 mmol) and 2.5 g of NiCl$_2$(PPh$_3$)$_2$ in 150 mL of THF was added over 1 hour 50 mL of neopentyl magnesium chloride (1.0 M in THF; 50 mmol). The mixture was stirred overnight and then quenched by adding 150 mL of 1.0 M aqueous hydrochloric acid. The product was isolated and purified (hexanes/silica) as for 2-benzyl-indene. Yield: 4.75 g, 66 percent $^1$H NMR (CDCl$_3$): δ 7.45–7.10 (m, 4H), 6.54 (s, 1H), 3.40 (s, 2H), 2.40 (s, 2H), 1.00 (s, 9H).

$^{13}$C {$^1$H} NMR (CDCl$_3$) δ 148.52, 145.93, 143.78, 129.61, 126.43, 123.82, 123.48, 120.14, 45.54, 43.88, 32.08, 30.17.

(2-neopentylinden-1-yl)-N-(1,1-dimethylethyl)dimethylsilanamine. To a mixture of 2-neopentylindene (0.81 g, 4.3 mmol) in 30 mL of hexanes were added 2.9 mL of butyl lithium (1.6 M hexane; 4.7 mmol). The mixture was stirred for one hour, diluted with 20 mL of THF and to this added N-(1,1-dimethylethyl)dimethylsilanamine chloride (1.84 g, 11.2 mmol) in 10 mL of THF. After stirring overnight, the volatiles were removed in vacuo, the residue extracted with hexane, filtered and the volatiles removed in vacuo to give 1.4 g (102 percent) of a yellow oil.

$^1$H NMR (C$_6$D$_6$): δ 7.41 (d, 1H), 7.33 (d, 1H), 7.20–7.00 (m, 2H), 6.50 (s, 1H), 3.44 (s, 1H), 2.62 (d, 1H), 2.38 (d, 1H), 1.04 (s, 9H), 0.87 (s, 9H), 0.02 (s, 3H), −0.14 (s, 3H);

$^{13}$C {$^1$H} NMR (C$_6$D$_6$) δ 149.83, 145.10, 144.49, 128.16, 127.45, 123.36, 122.59, 120.14, 51.84, 49.45, 44.78, 33.75, 33.75, 30.17, 1.17, −0.11.

(2-neopentylinden-1-yl)-N-(1,1-dimethylethyl)dimethylsilanamide titanium (IV) dichloride. A 125 mL flask was charged with 1.22 g (3.9 mmol) of (2-neopentylinden-1-yl)-N-(1,1-dimethylethyl)dimethylsilanamine and 30 mL of hexanes. To this was added over five minutes 4.9 mL of n-butyl lithium in hexanes (7.8 mmol, 1.6M). After 1 hour, 30 mL of THF was added and the solution cooled to −30° C. To this was added 1.43 g (3.9 mmol) of TiCl$_3$(THF)$_3$ and the solution allowed to warm to room temperature. After 45 minutes, 1.1 g (3.9 mmol) of PbCl$_2$ and 10 mL of dichloromethane were added. The solution was allowed to stir at room temperature for two hours and the volatiles were removed in vacuo. The residue was extracted into toluene, filtered and the volatiles removed in vacuo. The residue was triturated with hexanes and cooled to −30° C. The precipitate was isolated by filtration and the solid washed twice with 1 mL of cold hexanes. The solid was dried in vacuo to leave 0.79 g of orange powder. A second crop of material (200 mg) was obtained by concentration of the mother liquor and cooling at −30° C. overnigh—the NMR spectra of both crops were practically identical. Total yield: 0.99 g, 60 percent $^1$H NMR (C$_6$D$_6$): δ 7.64 (d, 1H), 7.26 (d, 1H), 7.10–6.80 (m, 3H), 2.74 (d, 1H), 2.63 (d, 1H), 1.31 (s, 9H), 0.77 (s, 9H), 0.57 (s, 3H), 0.54 (s, 3H);

$^{13}$C {$^1$H} NMR (C$_6$D$_6$) δ 148.05, 136.69, 134.80, 128.55, 127.91, 127.17, 126.27, 121.97, 62.43, 46.50, 32.85, 32.23, 29.59, 6.19, 5.70.

Example 10

(2-neopentylinden-1-yl)-N-(1,1-dimethylethyl)dimethyl-silanamide titanium (IV) dimethyl A 50 mL jar was charged with 150 mg (0.35 mmol) of (2-neopentylinden-1-yl)-N-(1,1-dimethylethyl)dimethylsilanamine titanium (IV) dichloride and 10 mL of diethyl ether. The mixture was cooled to −30° C. and to this added 0.30 mL of methyl magnesium bromide (0.9 mmol, 3.0 M in ether). After stirring and warming to room temperature over 1 hour, the volatiles were removed in vacuo and the residue extracted into 20 mL of hexanes. The extract was filtered through diatomaceous earth and the volatiles removed in vacuo. The residue was extracted into 20 mL of hexanes, filtered and the volatiles removed in vacuo to leave 119 mg of material (87 percent).

$^1$H NMR (C$_6$D$_6$): δ 7.51 (m, 2H), 7.02 (d, 1H), 6.85 (m, 2, ), 2.51 (d, 1H), 2.24 (d, 1H), 1.44 (s, 9H), 0.89 (s, 9H), 0.84 (s, 3H), 0.55/0.54 (2s, 6H), −0.15 (s, 3H);

$^{13}$C {$^1$H} NMR (C$_6$D$_6$) δ 144.41, 134.50, 131.90, 127.42, 125.58, 125.52, 125.07, 116.32, 58.05, 57.14, 52.58, 45.32, 34.25, 32.57, 29.83, 7.21, 6.55.

Example 11

(2.2-dimethylpropan-1-yl)inden-1-yl)-N-(1,1-dimethylethyl)diphenyl-silanamide titanium (IV) dichloride

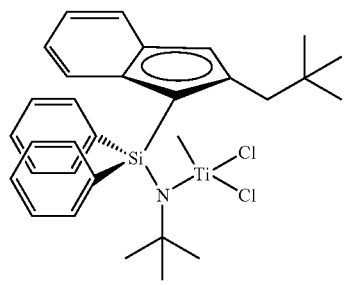

N-(1,1-dimethylethyl)diphenylsilanamine triflate. A 75 mL acetonitrile solution of silver triflate (4.88 g, 19 mmol) was vigorously stirred as a 75 mL acetonitrile solution of N-(1,1-dimethylethyl)dimethylsilanamine chloride (5.01 g, 17 mmol) was added over two minutes. After stirring for one hour, the volatiles were removed in vacuo and the residue extracted into toluene, filtered and the volatiles removed in vacuo. The residue was dried in vacuo to leave 6.86 g of product as an oily solid.

$^1$H NMR (C$_6$D$_6$): δ 7.62 (m, 4H), 7.05 (m, 6H), 1.03 (s, 9H);

$^{19}$F NMR (C$_6$D$_6$) δ −77.47.

(2-neopentylinden-1-yl)-N-(1,1-dimethylethyl)diphenyl-silanamine. To a mixture of 2-neopentylindenyl lithium (1.42 g, 7.4 mmol) in 25 mL of THF was added a 20 mL THBF solution containing 2.85 g (7.0 mmol) of N(1,1-dimethylethyl)diphenylsilanamine triflate. After stirring overnight, the volatiles were removed in vacuo, the residue extracted with a 1:1 mixture of hexanes:toluene, filtered and the volatiles removed in vacuo to give 3.1 g (100 percent) of a oily solid.

$^1$H NMR (C$_6$D$_6$): δ 7.654 (d, 2H), 7.48 (d, 2H), 7.2–7.05 (m, 8H), 6.95 (m, 1H), 6.29 (s, 1H), 4.03 (s, 1H), 2.41 (d, 1H), 2.27 (d, 1H), 1.01 (s, 9H), 0.81 (s, 9H);

$^{13}$C {$^1$H} NMR (C$_6$D$_6$) δ 148.83, 145.45, 144.18, 136.09, 135.99, 135.14, 129.56, 129.45, 129.15, 127.42, 127.27, 125.27, 124.01, 122.57, 120.23, 50.12, 49.25, 44.85, 33.53, 32.02, 29.93.

(2,2-dimethylpropan-1-yl)inden-1-yl)-N-(1,1-dimethylethyl)diphenylsilanamide titanium IV) dichloride. A 125 mL flask was charged with 2.66 g (6.1 mmol) of (2-neopentyl-inden-1-yl)-N-(1,1-dimethylethyl)diphenylsilanamine and 25 mL of hexanes. To this was added over five minutes 7.6 mL of n-butyl lithium in hexanes (12 mmol, 1.6M). After 1 hour, 25 mL of THF was added and the solution cooled to −30° C. To this was added 2.25 g (6.0 mmol) of TiCl$_3$(THF)$_3$ and the solution allowed to warm to room temperature. After 45 minutes, 1.7 g (6.1 mmol) of PbCl$_2$ and 10 mL of dichloromethane were added. The solution was allowed to stir at room temperature overnight and then the volatiles were removed in vacuo. The residue was extracted into diethyl ether, filtered and the volatiles removed in vacuo. The residue was triturated with hexanes (10 mL) and cooled to −30° C. The mother liquor was decanted and the solid washed twice with 2 ml of cold hexanes. The solid was dried in vacuo to leave 2.08 g (62 percent) of orange powder.

$^1$H NMR (C$_6$D$_6$): δ 8.14 (m, 2H), 7.69 (m, 2H), 7.40–6.95 (m, 9H), 6.77 (s, 1H), 6.55 (m, 1H), 2.6 (d, 1H), 2.52 (d, 1H), 1.56 (s, 9H), 0.55 (s, 9H).

$^{13}$C {$^1$H} NMR (C$_6$D$_6$) δ 148.74, 137.61, 136.83, 136.31, 135.98, 135.73, 135.40, 130.78, 130.64, 129.80, 127.97, 126.57, 125.99, 121.83, 61.89, 45.70, 33.12, 32.44, 29.27.

Example 12

(2,2-dimethylpropan-1-yl)inden-1-yl)-N-(1,1-dimethylethyl)diphenyl-silanamide titanium (IV) dimethyl A 50 mL jar was charged with 137 mg (0.25 mmol) of (2-neopentylinden-1-yl)-N-(1,1-dimethylethyl)diphenylsi-lanamide titanium (IV) dichloride and 10 mL of diethyl ether. The mixture was cooled to −30° C. and to this added 0.20 ml of methyl magnesium bromide (0.62 mmol, 3.0 M in ether). After stirring and warming to room temperature over 1 hour, the volatiles were removed in vacuo and the residue extracted into 20 ml of hexanes. The extract was filtered through diatomaceous earth and the volatiles removed in vacuo. The residue was extracted into 20 ml of hexanes, filtered and the volatiles removed in vacuo to leave 85 mg of material (67 percent).

$^1$H NMR (C$_6$D$_6$): δ 8.19 (m, 2H), 7.65 (m, 2H), 7.43 (d, H), 7.30–6.90 (m, 9H), 6.86 (s, 1H), 6.50 (m, 1H), 2.21 (d, 1H), 2.12 (d, 1H), 1.66 (s, 9H), 1.17 (s, 3H), 0.63 (s, 9H), −0.03 (s, 3H);

$^{13}$C {$^1$H} NMR (C$_6$D$_6$) δ 143.88, 138.64, 137.63, 137.34, 136.04, 135.07, 132.22, 129.93, 129.84, 128.39, 127.78, 127.62, 125.58, 125.33, 124.15, 117.35, 61.68, 57.41, 55.16, 44.43, 34.97, 32.14, 29.73.

Polymerization General Conditions

Mixed alkanes and liquid olefins are purified by sparging with purified nitrogen followed by passage through columns containing alumina (A-2, available from LaRoche Inc.) and Q5 reactant (available from Englehard Chemicals Inc.) at 50 psig (450 kPa) using a purified nitrogen pad. All transfers of solvents and solutions described below are accomplished using a gaseous pad of dry, purified nitrogen or argon. Gaseous feeds to the reactor are purified by passage through columns of A-204 alumina (available from LaRoche Inc.) and Q5 reactant. The aluminas are previously activated by treatment at 375° C. with nitrogen, and Q5 reactant is activated by treatment at 200° C. with 5 percent hydrogen in nitrogen.

Polymerization 1

A stirred, two-liter Parr reactor was charged with 740 g of mixed alanes and 118 g of purified 1-octene comonomer. Hydrogen (25 psi (170 kPa), 5.7 mmoles) was added as a molecular weight control agent by differential pressure expansion from a 75 mL addition tank at 300 psig (2.2 MPa). The reactor was heated to 140° C. and saturated with ethylene at 500 psig (3.5 MPa). The appropriate amount of catalyst and cocatalyst (either methyldi($C_{14-18}$alkyl)ammoniumtetralis(penta-fluorophenyl)borate (MDPB) or trispentafluorophenylborane (FAB)) as 0.005M solutions in toluene were premixed in a glovebox and transferred to a catalyst addition tank and injected into the reactor. The polymerization conditions were maintained during the run with ethylene on demand.

After 15 minutes reaction time, the resulting solution was removed from the reactor into a nitrogen purged collection vessel containing 100 ml of isopropyl alcohol and 20 ml of a 10 weight percent toluene solution of hindered phenol antioxidant (Irganox™ 1010 from Ciba Geigy Corporation) and phosphorus stabilizer (Irgafos™ 168 from Ciba Geigy Corporation). Polymers formed are dried in a programmed vacuum oven with a maximum temperature of 145° C. and a 20 hour heating period. The results are contained in Table 1.

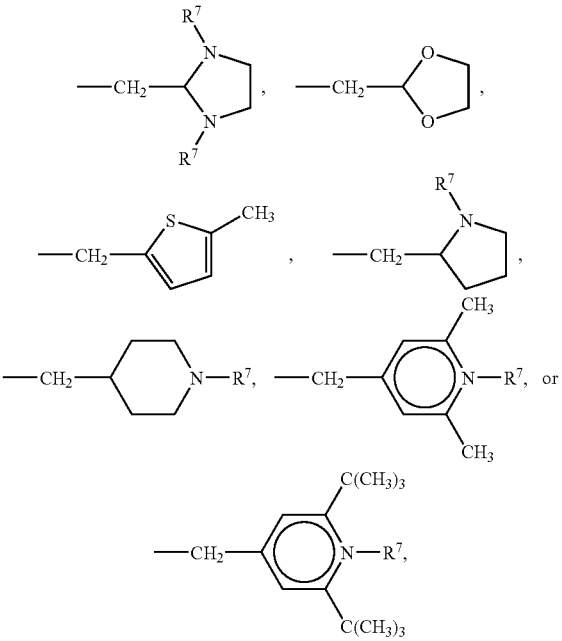

wherein $R^7$ is hydrogen or $C_{1-10}$ alkyl,
  said group containing 2 or 3 non-hydrogen substituents on at least one β-position thereof;
  M is a metal selected from Groups 3–10 or the Lanthanide series of the Periodic Table of the Elements;
  Z is a divalent moiety of the formula -Z'Y— joining Cp and M, wherein,
  Y is —O—, —S—, —$NR^5$—, —$PR^5$, —$NR^5_2$, or —$PR^5_2$;
  Z' is $SiR^6_2$, $CR^6_2$, $SiR^6_2SiR^6_2$, $CR^6_2CR^6_2$, $CR^6$=$CR^6$, $CR^6_2SiR^6_2$, $BR^6$, or $GeR^6_2$, bound at the 1-position of Cp;

TABLE 1

| Run | Catalyst µmoles | Cocatalyst (µmoles) | Yield (g) | Efficiency (g/µg Ti) | Density (g/mL) | MMI[1] | Mw[2] | MWD[2] |
|---|---|---|---|---|---|---|---|---|
| 1 | Ex. 2 (1.0) | MDPB (1.0) | 77.5 | 1.47 | 0.875 | 11.8 | 62,300 | 2.2 |
| 2 | Ex. 2 (1.1) | FAB (1.1) | 29.7 | 0.56 | 0.876 | 8.9 | 64,800 | 2.2 |
| 3 | Ex. 4 (1.0) | MDPB (1.0) | 86.4 | 2.26 | 0.876 | 2.0 | 98,200 | 2.2 |
| 4 | Ex. 4 (0.5) | FAB (0.5) | 25.8 | 1.08 | 0.884 | 1.0 | 83,500 | 4.4 |
| 5 | Ex. 6 (0.4) | MDPB (0.4) | 39.9 | 2.08 | 0.873 | 8.2 | 70,200 | 2.2 |
| 6 | Ex. 8 (0.3) | MDPB (0.3) | 31.6 | 2.20 | 0.881 | 1.3 | 109,000 | 2.1 |
| 7 | Ex. 10 (0.3) | MDPB (0.3) | 76.9 | 5.40 | 0.872 | 2.8 | 85,500 | 2.5 |
| 8 | Ex. 10 (1.4) | FAB (1.4) | 59.7 | 0.90 | 0.876 | 2.6 | 90,900 | 2.1 |
| 9 | Ex. 12 (0.4) | MDPB (0.4) | 75.6 | 3.95 | 0.874 | 0.8 | 124,000 | 2.3 |
| 10 | Ex. 12 (1.3) | FAB (1.3) | 43.6 | 0.70 | 0.875 | 0.5 | 137,000 | 2.3 |

[1] melt index as determined by micromelt technique
[2] Mw and MWD (molecular weight distribution) determined by GPC analysis

The invention claimed is:

1. A metal compound corresponding to the formula:

$$CpM(Z)_z(X)_x(T)_t(X')_{x'} \qquad (I),$$

Cp is a substituted inden-1-yl or partially hydrogenated derivative thereof substituted at least at the 2-position thereof with a $C^{4-30}$ alkyl, aralkyl, or trihydrocarbylsilylhydrocarbyl group, or a Group 15 or 16 heteroatom containing group corresponding to the formula:

$R^5$, independently each occurrence, is hydrocarbyl, trihydrocarbylsilyl, or trihydrocarbylsilylhydrocarbyl, said $R^5$ having up to 20 atoms other than hydrogen, and optionally two $R^5$ groups or $R^5$ together with Y form a ring system;

$R^6$, independently each occurrence, is hydrogen, or a member selected from hydrocarbyl, hydrocarbyloxy, silyl, halogenated alkyl, halogenated aryl, —$NR^5_2$, and combinations thereof, said $R^6$ having up to 30 non-hydrogen atoms, and optionally, two $R^6$ groups form a ring system;

X is hydrogen or a monovalent anionic ligand group having up to 60 atoms not counting hydrogen;

T independently each occurrence is a neutral ligating compound having up to 20 atoms, other than hydrogen, and optionally T and X are bonded together;

X' is a divalent anionic ligand group having up to 60 atoms other than hydrogen;

z is 0, 1 or 2;

x is 0, 1, 2, or 3;

t is a number from 0 to 2, and x' is 0 or 1.

2. A metal compound according to claim 1 corresponding to the formula:

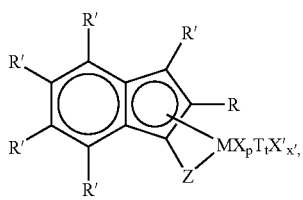
(II)

wherein:

R' independently each occurrence is hydrogen, hydrocarbyl, trihydrocarbylsilyl, trihydrocarbylgermyl, halide, hydrocarbyloxy, trihydrocarbylsiloxy, bis(trihydrocarbylsilyl)amino, di(hydrocarbyl)amino, hydrocarbyleneamino, hydrocarbylimino, di(hydrocarbyl)phosphino, hydrocarbylenephosphino, hydrocarbylsulfido, halo-substituted hydrocarbyl, hydrocarbyloxy-substituted hydrocarbyl, trihydrocarbylsilyl-substituted hydrocarbyl, trihydrocarbylsiloxy-substituted hydrocarbyl, bis(trihydrocarbylsilyl)amino-substituted hydrocarbyl, di(hydrocarbyl)amino-substituted hydrocarbyl, hydrocarbyleneanilno-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said R' group having up to 40 atoms not counting hydrogen atoms, and two R' groups together may form a divalent derivative thereby forming a saturated or unsaturated ring;

R is a $C_{4-12}$ alkyl, aralkyl, or trihydrocarbylsilylhydrocarbyl group, or a Group 15 or 16 heteroatom containing group corresponding to the formula:

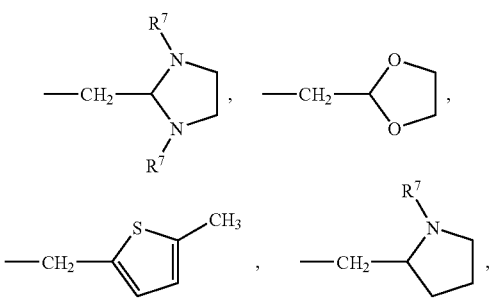

-continued

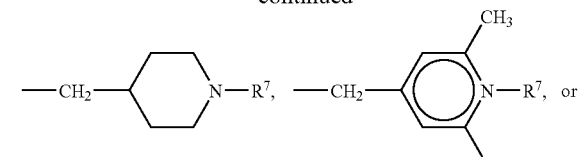

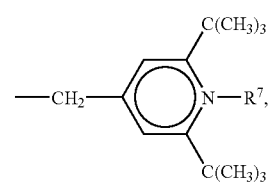

wherein $R^7$ is hydrogen or $C_{1-10}$ alkyl, said R group containing 2 or 3 non-hydrogen substituents at the β-position thereof;

M is a Group 4 metal;

Z is -Z'-Y—;

Y is —O—, —S—, —NR$^5$—, —PR$^5$—, —NR$^5_2$, or —PR$^5_2$;

Z' is $SiR^6_2$, $CR^6_2$, $SiR^6_2SiR^6_2$, $CR^6_2CR^6_2$, $CR^6=CR^6$, $CR^6_2SiR^6_2$, $BR^6$, or $GeR^6_2$;

$R^5$ each occurrence is independently hydrocarbyl, trihydrocarbylsilyl, or trihydrocarbylsilyihydrocarbyl, said $R^5$ having up to 20 atoms other than hydrogen, and optionally two $R^5$ groups or $R^5$ together with Y form a ring system;

$R^6$ each occurrence is independently hydrogen, or a member selected from hydrocarbyl, hydrocarbyloxy, silyl, halogenated ailcyl, halogenated aryl, —NR$^5_2$, and combinations thereof, said $R^6$ having up to 20 non-hydrogen atoms, and optionally, two $R^6$ groups form a ring system;

X, T, and X' are as previously defined in claim 1;

x is 0, 1 or 2;

t is 0 or 1; and x' is 0 or 1.

3. A metal compound according to claim 1, corresponding to the formula:

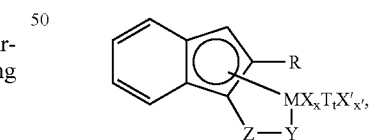

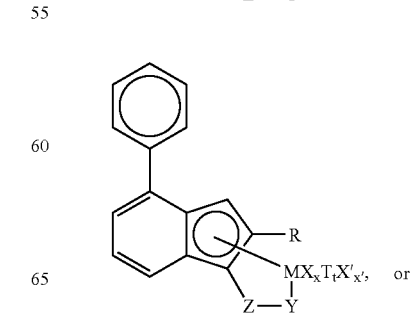

-continued

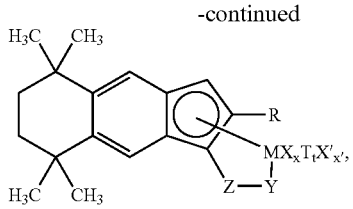

wherein

M is titanium;

R is 2,2-dimethylpropan-1-yl, 2-methyl-2-phenylpropan-1-yl, benzyl, or parafluorophenylmethyl;

Y is —O—, —S—, —NR$^5$—, —PR$^5$—, —NR$^5_2$, or —PR$^5_2$;

Z' is SiR$^6_2$, CR$^6_2$, SiR$^6_2$SiR$^6_2$, CR$^6_2$CR$^6_2$, CR$^6$=CR$^6$, CR$^6_2$SiR$^6_2$, BR$^6$, or GeR$^6_2$;

R$^5$ each occurrence is independently hydrocarbyl, trihydrocarbylsilyl, or trihydrocarbylsilylhydrocarbyl, said R$^5$ having up to 20 atoms other than hydrogen, and optionally two R$^5$ groups or R$^5$ together with Y form a ring system;

R$^6$ each occurrence is independently hydrogen, or a member selected from hydrocarbyl, hydrocarbyloxy, silyl, halogenated alkyl, halogenated aryl, —NR$^5_2$, and combinations thereof, said R$^6$ having up to 20 non-hydrogen atoms, and optionally, two R$^6$ groups form a ring system;

X, T, and X' are as previously defined in claim 1;

x is 0, 1 or 2;

t is 0 or 1; and x' is 0 or 1;

and, when x is 2, x' is zero, M is in the +4 formal oxidation state or M is in the +3 formal oxidation state if Y is —NR$^5_2$ or —PR$^5_2$, and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy-, and di(hydrocarbyl)phosphino-Substituted derivatives thereof, said X group having up to 30 atoms not counting hydrogen, when x is 0 and x' is 1, M is in the +4 formal oxidation state, and X' is a dianionic ligand selected from the group consisting of hydrocarbadiyl, oxyhydrocarbylene, and hydrocarbylenedioxy groups, said X' group having up to 30 nonhydrogen atoms, when x is 1, and x' is 0, M is in the +3 formal oxidation state, and X is a stabilizing anionic ligand group selected from the group consisting of allyl, 2-(N,N-dimethylamino)phenyl, 2-(N,N-dimethylaminomethyl)phenyl, and 2-(N,N-dimethylamino)benzyl, and when x and x' are both 0, t is 1, M is in the +2 formal oxidation state, and T is a neutral, conjugated or nonconjugated diene, optionally substituted with one or more hydrocarbyl groups, said T having up to 40 carbon atoms and being bound to M by means of delocalized π-electrons thereof.

4. A metal complex according to claim 1 selected from the group consisting of:

(2-neopentylinden-1-yl)-N-( 1,1-dimethylethyl)dimethyl-silanamide titanium (IV) dimethylenedimethylsilane, (2-neopentylinden-1-yl)-N-(1,1-dimethylethyl)dimethyl-silanamide titanium (II) 1,3-pentadiene, (2-neopentylinden-1-yl)-N-(1,1-dimethylethyl)dimethyl-silanamide titanium (III) 2-(N,N-dimethylamino)benzyl, (2-neopentylinden-1-yl)-N-(1,1-dimethylethyl)dimethyl-silanamide titanium (IV) dichioride, (2-neopentylinden-1-yl)-N-(1,1-dimethylethyl)dimethyl-silanamide titanium (IV) dimethyl, (2-neopentylinden-1-yl)-N-(1,1-dimethylethyl)dimethyl-silanamide titanium (IV) dibenzyl, (2-(parafluorophenylmethyl)inden-1-yl)-N-(1,1-dimethylethyl)dimethylsilanamide titanium (IV) dimethylenedimethylsilane, (2-(parafluorophenylmethyl)inden-1-yl)-N-(1,1-dimethylethyl)dimethylsilanamide titanium (II) 1,3-pentadiene, (2-(parafluorophenylmethyl)inden-1-yl)-N-(1,1-dimethylethyl)dimethylsilanamide titanium (III) 2-(N,N-dimethylamino)benzyl, (2-(parafluorophenylmethyl)inden-1-yl)-N-(1,1-dimethylethyl)dimethylsilanamide titanium (IV) dichioride, (2-(parafluorophenylmethyl)inden-1-yl)-N-(1,1-dimethylethyl)dimethylsilanamide titanium (IV) dimethyl, (2-(parafluorophenylmethyl)inden-1-yl)-N-(1,1-dimethylethyl)dimethylsilananude titanium (IV) dibenzyl, (2-beuzylinden-1-yl)-N-(1,1-dimethylethyl)dimethylsilanamide titanium (IV) dimethylenedimethylsilane, (2-benzylinden-1-yl)-N-(1,1-dimethylethyl)dimethylsilanamide titanium (II) 1,3-pentadiene, (2-benzylinden-1-yl)-N-(1,1-dimethylethyl)dimethylsilanamide titanium (III) 2-(N,N-dimethylamino)benzyl, (2-benzylinden-1-yl)-N-(1,1-dimethylethyl)dimethylsilanamide titanium (IV) dichioride, (2-benzylinden-1-yl)-N-(1,1-dimethylethyl)dimethylsilanamide titanium (IV) dimethyl, (2-benzylinden-1-yl)-N-(1,1-dimethylethyl)dimethylsilanamide titanium (IV) dibenzyl, (2-(2,2-dimethyl-1-butylinden-1-yl)-N-(1,1-dimethylethyl)dimethylsilanamide titanium (IV) dimethylenedimethylsilane, (2-(2,2-dimethyl-1-butylinden-1-yl)-N-(1,1-dimethylethyl)dimethylsilanamide titanium (II) 1,3-pentadiene, (2-(2,2-dimethyl-1-butylinden-1-yl)-N-(1,1-dimethylethyl)dimethylsilanamide titanium (III) 2-(N,N-dimethylamino)benzyl, (2-(2,2-dimethyl-1-butylinden-1-yl)-N-(1,1-dimethylethyl)dimethylsilanamide titanium (IV) dichioride, (2-(2,2-dimethyl-1-butylinden-1-yl)-N-(1,1-dimethylethyl)dimethylsilanamide titanium (IV) dimethyl, (2-(2,2-dimethyl-1-butylinden-1-yl)-N-(1,1-dimethylethyl)dimethylsilanamide titanium (IV) dibenzyl, and mixtures thereof.

5. An olefin polymerization process comprising contacting one or more olefin monomers under polymerization conditions with a catalyst composition comprising a metal complex according to any one of claims 1–4.

6. The process of claim 5 wherein the catalyst composition additionally comprises an activating cocatalyst.

7. The process of claim 5 conducted under solution, slurry or high pressure polymerization conditions.

8. The process of claim 5 conducted under slurry or gas phase polymerization conditions, wherein the catalyst additionally comprises an inert, particulated support.

9. The process of claim 6 wherein the activating cocatalyst is: trispentafluorophenylborane, methylditetradecylanimonium tetrakis(pentafluorophenyl)borate, (pentafluorophenyl)ditetradecylammoflium tetrakis(pentafluorophenyl)borate, dimethyltetradecylammonium tetrakis(pentafluorophenyl)borate, methyldihexadecyl-animonium tetrakis(pentafluorophenyl)borate, (pentafluorophenyl)dihexadecylammonium tetrakis(pentafluorophenyl)borate, dimethylhexadecylammonium tetrakis(pentafluorophenyl)-borate, methyldioctadecylammonium tetrakis(pentafluorophenyl)borate, (pentafluorophenyl)dioctadecylammomum tetrakis(pentafluorophenyl)borate, dimethyloctadecylammonium tetrakis(pentafluorophenyl)borate, methylalumoxane, triisobutylaluminum modified methylalumoxane, or a mixture thereof.

* * * * *